US010664572B2

(12) United States Patent
Bitran et al.

(10) Patent No.: US 10,664,572 B2
(45) Date of Patent: May 26, 2020

(54) RECOMMENDATIONS FOR HEALTH BENEFIT RESOURCES

(71) Applicant: Microsoft Technology Licensing, LLC, Redmond, WA (US)

(72) Inventors: Hadas Bitran, Ramat Hasharon (IL); Todd Holmdahl, Redmond, WA (US); Eric Horvitz, Kirkland, WA (US); Desney S. Tan, Kirkland, WA (US); Dennis Paul Schmuland, Redmond, WA (US); Adam T. Berns, Issaquah, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 668 days.

(21) Appl. No.: 14/970,098

(22) Filed: Dec. 15, 2015

(65) Prior Publication Data

US 2017/0039344 A1 Feb. 9, 2017

Related U.S. Application Data

(60) Provisional application No. 62/202,115, filed on Aug. 6, 2015.

(51) Int. Cl.
*G06F 19/00* (2018.01)
*G06Q 50/24* (2012.01)
(Continued)

(52) U.S. Cl.
CPC ......... *G06F 19/3475* (2013.01); *G06Q 40/08* (2013.01); *G06Q 50/22* (2013.01);
(Continued)

(58) Field of Classification Search
CPC .... G06F 19/3475; G16H 10/60; G16H 20/10; G16H 20/60; G16H 20/70; G16H 50/20;
(Continued)

(56) References Cited

U.S. PATENT DOCUMENTS

| 8,423,378 B1 | 4/2013 | Goldberg |
| 8,781,849 B1 | 7/2014 | Grossman |

(Continued)

FOREIGN PATENT DOCUMENTS

| CA | 2616111 C | 2/2007 |
| CN | 103699764 A | 4/2014 |

(Continued)

OTHER PUBLICATIONS

Jepsen, IT in Healthcare: Progress Report, Feb. 2003, IT Pro IEEE Computer Society, pp. 8-14. (Year: 2003).*

(Continued)

*Primary Examiner* — Christopher L Gilligan
(74) *Attorney, Agent, or Firm* — Alleman Hall Creasman & Tuttle LLP

(57) ABSTRACT

A computing system comprises an electronic personal assistant application program executed on a client computing device. Included are a health insurance retriever configured to retrieve health insurance information of a user, a history combiner configured to combined aggregated histories of a plurality of users into an anonymized combined time and location-based data, and a health recommender configured to identify at least one health condition of the user, determine a health recommendation at least on the identified health condition, and output the health recommendation including the recommended health care service, providers, and an indication of insurance coverage of the recommended service at each of the providers.

20 Claims, 13 Drawing Sheets

(51) Int. Cl.
  *G06Q 50/22* (2018.01)
  *G16H 10/60* (2018.01)
  *G16H 20/60* (2018.01)
  *G16H 20/10* (2018.01)
  *G16H 50/20* (2018.01)
  *G16H 40/63* (2018.01)
  *G16H 20/70* (2018.01)
  *G16H 40/20* (2018.01)
  *G06Q 40/08* (2012.01)

(52) U.S. Cl.
  CPC .............. *G06Q 50/24* (2013.01); *G16H 10/60* (2018.01); *G16H 20/10* (2018.01); *G16H 20/60* (2018.01); *G16H 20/70* (2018.01); *G16H 40/20* (2018.01); *G16H 40/63* (2018.01); *G16H 50/20* (2018.01)

(58) Field of Classification Search
  CPC ........ G16H 40/20; G16H 40/63; G06Q 40/08; G06Q 50/24; G06Q 50/22
  See application file for complete search history.

(56) References Cited

U.S. PATENT DOCUMENTS

| | | | |
|---|---|---|---|
| 2009/0006994 A1* | 1/2009 | Forstall | G01C 21/20 715/764 |
| 2010/0082369 A1 | 4/2010 | Prenelus et al. | |
| 2013/0325404 A1* | 12/2013 | Yuen | G06F 11/00 702/182 |
| 2014/0006053 A1 | 1/2014 | Moen et al. | |
| 2014/0114677 A1 | 4/2014 | Holmes | |
| 2014/0136233 A1 | 5/2014 | Atkinson et al. | |
| 2014/0201095 A1 | 7/2014 | Kusens | |
| 2014/0236630 A1 | 8/2014 | Murata | |
| 2014/0244310 A1 | 8/2014 | Kay | |
| 2014/0257836 A1 | 9/2014 | Walker et al. | |
| 2014/0275854 A1 | 9/2014 | Venkatraman et al. | |
| 2014/0278449 A1 | 9/2014 | Kharraz Tavakol | |
| 2014/0297318 A1* | 10/2014 | Prasad | G06Q 50/24 705/3 |
| 2015/0100326 A1 | 4/2015 | Kowalkiewicz et al. | |
| 2015/0193580 A1 | 7/2015 | Mosier et al. | |
| 2015/0370981 A1* | 12/2015 | Nuckolls | G06F 19/345 705/2 |
| 2016/0012193 A1* | 1/2016 | Almogy | G06F 19/00 705/3 |
| 2016/0132697 A1* | 5/2016 | Simske | G06F 21/6254 726/26 |

FOREIGN PATENT DOCUMENTS

| | | |
|---|---|---|
| KR | 20140038732 A | 3/2014 |
| KR | 101439809 B1 | 9/2014 |
| WO | 2013066642 A1 | 5/2013 |

OTHER PUBLICATIONS

Ackerman et al., Telemedicine Technology, 2002, Telemedicine Journal and e-Health, vol. 8, No. 1, pp. 71-78. (Year: 2002).*
ISA European Patent Office, International Search Report and Written Opinion Issued in Application No. PCT/US2016/043224, dated Sep. 23, 2016, WIPO, 11 Pages.
"Myhealthrecords.in", Published on: Feb. 12, 2012 Available at: http://www.myhealthrecords.in/MHR5.2/static/.
"HealthVault", Retrieved on: Aug. 7, 2015 Available at: https://www.healthvault.com/in/en/overview#Prepare.
Buytendijk, F. et al., "Summary and Link to Purchase 'Analytics Gets Personal with the Quantified Self'," Gartner, Inc. Website, Available Online at https://www.gartner.com/doc/2487617?ref=ddisp, May 17, 2013, 2 pages. (Applicant finds no readily available full copy; USPTO encouraged to obtain its own copy).
McIntyre, A. et al., "Summary and Link to Purchase 'Market Trends: Enter the Wearable Electronics Market With Products for the Quantified Self'," Gartner, Inc. Website, Available Online at https://www.gartner.com/doc/2537715?ref=ddisp, Jul. 1, 2013, 2 pages. (Applicant finds no readily available full copy; USPTO encouraged to obtain its own copy).
Gotta, S., "Summary and Link to Purchase 'Technology Overview: Quantified Self'," Gartner, Inc. Website, Available Online at https://www.gartner.com/doc/2591327?ref=ddisp, Sep. 17, 2013, 2 pages. (Applicant finds no readily available full copy; USPTO encouraged to obtain its own copy).
Dunbrack, L., "Abstract and Link to Purchase 'Perspective: The Consumer Experience—Why Consumers Stop Using Fitness Trackers'," IDC Research, Inc. Website, Available Online at http://www.idc.com/getdoc.jsp?containerId=HI249613, Jun. 2014, 2 pages. (Applicant finds no readily available full copy; USPTO encouraged to obtain its own copy).

* cited by examiner

100

☰
⌂
▭
▭
👤

😃
Hi Hadas! You just visited
Dr. Smith today.

See all specialties

| JBS | Dr. John B. Smith, M.D. | 2015 |
| | Internal Medicine | 10/5 |
| | Seen at 9:00-9:15am | MON |

— 104

How would you rate your satisfaction with Dr. John B. Smith for this visit?

☐ Extremely satisfied

☐ Very satisfied

☐ Somewhat satisfied

☐ Unsatisfied

☐ Very unsatisfied

NEXT PAGE

☆ Ask me anything 🎤

FIG. 5

RECOMMENDATIONS FOR HEALTH BENEFIT RESOURCES

CROSS REFERENCE TO RELATED APPLICATIONS

This application claims priority to U.S. Provisional Patent Application No. 62/202,115, filed Aug. 6, 2015, the entirety of which is hereby incorporated herein by reference.

BACKGROUND

Improving one's health is a goal that most individuals share, yet many people fall short in achieving. In our busy lives, it can be difficult to make needed health-promoting lifestyle changes and make time to visit health care providers for acute care, checkups, health & wellness programs, guidance, and preventative care. And, many people have trouble following through with resolutions to eat well and exercise. It can also be difficult for people who are not feeling well to navigate and discover health benefit resources they are entitled to that are often disorganized or buried in human resources or health insurance portals or documents. Once a symptom or concerning diagnosis is issued, finding the multiplicity of resources and professionals available under a health insurance plan can be arduous and frustrating. Significant challenges exist to improving the health and well-being of both individuals and entire populations by promptly connecting them to the resources they are entitled to through multiple accessible channels, including apps, web, voice, text, or chat, which the technological solutions described herein offer the promise of addressing.

SUMMARY

A computing system is provided that includes an electronic personal assistant application program executed on a client computing device. The electronic personal assistant application program includes a health recommender configured to identify at least one health condition of the user, determine a health recommendation, including at least a recommended health care service, at least based on the identified health condition, the user's electronic medical record, and the user's geolocation data, identify a plurality of health care providers that deliver the recommended health care service in a vicinity of the user, and output the health recommendation, the plurality of health care providers, and an indication of whether the recommended health care service is covered by the user's health insurance plan at each of the plurality of health care providers. The electronic personal assistant application program may further include a health insurance retriever configured to retrieve the user's health insurance information, indicating whether the recommended health care service is covered by the user's health insurance plan at each of the plurality of health care providers.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

FIGS. 4 and 5 show an example appointment scheduling interface according to an embodiment of the present description.

DETAILED DESCRIPTION

Figure 1:
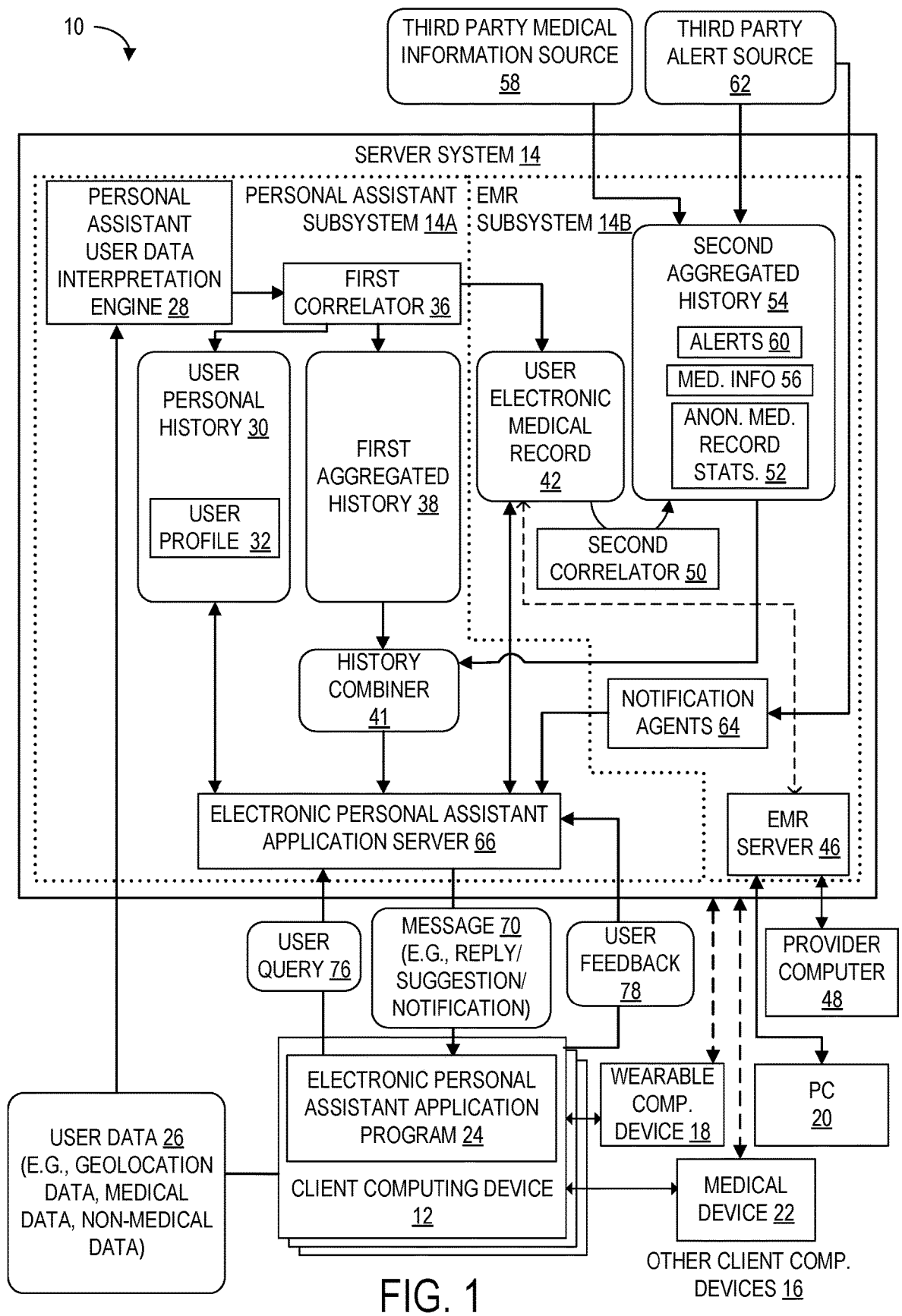
FIG. 1 illustrates a computing system according to one embodiment of the present disclosure.

FIG. 1 illustrates a computing system 10 according to one embodiment of the present disclosure. As shown, computing system 10 includes a client computing device 12, which, for example, may take the form of a smart phone or tablet computing device, configured to communicate via a computer network with a server system 14. Computing system 10 may also include other client computing devices 16 configured to communicate with the server system directly through a network connection or indirectly through the client computing device 12. The other client computing devices 16 may include a wearable computing device 18, which may take the form of a wrist mounted device or head mounted device, a personal computer 20, which may take the form of a laptop or desktop computer, and a computerized medical device 22, such as a computerized pulse oximeter, electronic inhaler, electronic insulin delivery device, electronic blood sugar monitor, blood pressure monitor, etc. Wearable computing devices may also include sensors embedded in clothing (t-shirts, undergarments, etc.), or mounted to other body parts (e.g., a finger or ear lobe). Also envisaged are IOT devices not worn directly on the body, but arranged in physical proximity to the user. Such devices may allow measurement of biometric and other data. Examples include cameras, far-infrared thermal detectors, and under-the-mattress sleep sensors, etc. Herein, where functions of the client computing device 12 are described, it will be appreciated that any of the other client computing devices 16 may function in the same manner, unless the specific form factor of the device is mentioned explicitly.

Client computing device 12 is configured to execute an electronic personal assistant application program 24. It will be appreciated that other instances of the electronic personal assistant application program 24 may be executed on the other client computing devices 16 as well, all of which are associated with a user account on server system 14. Subject to authorization by a user, the electronic personal assistant program 24 is configured to passively monitor various user data 26 on the client computing device 12 and other client computing devices 16, such as location data, search history, download history, browsing history, contacts, social network data, calendar data, biometric data, medical device data, purchase history, etc.

Specific examples of these various types of user data 26 will now be described. The user data 26 may comprise medical data, non-medical data, and geolocation data associated with the medical data and non-medical data. Geolocation data may include for example, GPS coordinate data (time stamp, latitude, longitude, and altitude) obtained by a GPS receiver implemented on any client computing device 12, medical device 22, or other client computing devices 16, an identifier such as an IP address and/or Wi-Fi access point identifier that can be resolved to a generalized geographic location, wireless triangulation, secondary devices such as cameras, other client computing devices, automobile devices, cell phone towers, a user check-in or log-in into computers or networks at locations such as points of service, stores, Wi-Fi hotspots, schools, hospitals, and clinics.

Non-medical data may include the following: search history may include a user's search queries entered in a search engine interface such as a browser displaying a search engine web page or a search application executed on the client computing device. The download history may include, for example, applications installed, or files downloaded from a download website, including songs, videos, games, etc. Each of these applications and files may have metadata associated with them, such as categories, genres, etc., which can be used to build user profile 32, discussed below. The browse history may include a list of websites, and particular pages within websites visited by a user using a browser executed on the client computing device. The browse history may also include in-application browsing of application specific databases, such as a shopping application that is configured to enable a user to browse a vendor's catalog. The contacts include names and contact information for individuals or organizations saved in a user contact database on client computing device 12, or retrieved from an external site, such as a social network website. The social network data may include a user's social media posts, friends list, a list of social network entities "liked" by the user, check-ins made by the user at locations via a social network program, posts written by the user, etc. Purchase history may include information gleaned from an ecommerce transaction between the client computing device 12 and an ecommerce platform, regarding products purchased by a user, including product descriptions, time and date of purchase, price paid, user feedback on those purchases, etc. The non-medical data may also comprise at least one of weather data, allergen concentration, pathogen concentration, UV index, and air quality (including air pollen and pollutant concentration measurements).

The medical data may comprise at least one of user's electronic medical record 42, biometric data, and medical device data. Biometric data may include a variety of data sensed by sensors on client computing device 12, medical device 22, or other client computing devices 16, such as pedometer information, heart rate and blood pressure, duration and timing of sleep cycles, body temperature, galvanic skin response, etc. Additional biometric data is discussed below in relation to the wristwatch embodiment of the wearable computing device 18. Medical device data may include data from medical device 22. Such data may include, for example, inhaler usage data from an electronic inhaler device, blood test results including blood sugar levels from an electronic blood sugar monitor, insulin pumping data from an electronic insulin pump, pulse oximetry data from an electronic pulse oximeter, gene expression data, etc. The blood test results may also comprise at least one of drug concentration, blood count, and metabolite concentration. It will be appreciated that these specific examples are merely illustrative and that other types of user data specifically not discussed above may also be monitored.

User data 26 is transmitted from the electronic personal assistant application program 24 to the personal assistant interpretation engine 28 executed on server system 14. The personal assistant user data interpretation engine 28 performs various operations on the received user data 26, including parsing and converting the user data 26 into a format and structure that enables the first correlator 36 to process the user data 26. The interpretation engine 28 may also isolate pieces of information from the non-medical data that are relevant to the health of the user. For example, the interpretation engine 28 may isolate reports of a user's illness in a social media post. After performing various operations on the user data 26, the interpretation engine 28 sends the user data 26 for each individual user to a first correlator 36.

The first correlator 36 is configured to correlate, with the aid of a processor, a plurality of medical and non-medical data 26 from a plurality of client computing devices 12 of a plurality of users with corresponding geolocation data to generate a first aggregated time and location-based history 38, which is subsequently stored in a mass storage device of the server system 14. The first correlator 36 is also configured to correlate a plurality of medical data and non-medical data of the user from the client computing device of the user with corresponding geolocation data and generate a user personal time and location-based history 30. The medical data and non-medical data are associated with time-stamped geolocation data. The personal history 30 includes a user profile 32 that is inferred by the first correlator 36 from the personal history 30 of the user. The first correlator 36 may input into the user electronic medical record 42 the user profile 32 and/or personal history 30 based on user settings 44 in the electronic personal assistant application server 66.

As a specific example, the user profile 32 may include inferred data from the user data 26 regarding the demographic data on the age, gender, race and ethnicity, and place of residence of the user, geographic travel history of the user, place of employment of the user, family unit of the user, family medical history, past medical history of the user, preexisting medical conditions of the user, current medications of the user, allergies of the user, surgical history, past medical screenings and procedures, past hospitalizations and visits, social history (alcohol, tobacco, and drug use, sexual history and habits, occupation, living conditions), health maintenance information (exercise habits, diet information, sleep data, vaccination data, therapy and counseling history), health provider preferences, and health insurance information.

User electronic medical records 42 are secure electronic records stored in a database in a mass storage device associated with server system 14. Typically, data is populated within the electronic medical record for each user by a healthcare provider using provider computer 48. Provider computer 48 interacts with secure electronic medical record server 46, which in turn stores and retrieves the data in the user electronic medical record 42. The EMR server is configured to communicate with secure channels (e.g., HTTPS and TLS), and store data in encrypted form. Further, the EMR server is configured to control access to the user electronic medical record such that only authorized healthcare providers can make entries and alter certain provider-controlled fields of the medical record. Provider controlled fields may include many of the same types of data included in the user profile, but which are confirmed with the user by the provider and entered into the medical record by the provider rather than inferred by computer algorithms, thus the accuracy and provenance of the data in the EMR is greater than the user profile 32. Specific examples of data that may be stored in the provider controlled portion of the user electronic medical record include demographic data on the age, gender, race and ethnicity, and place of residence of the user, geographic travel history of the user, place of employment of the user, family unit of the user, family medical history, past medical history of the user, preexisting medical conditions of the user, current medications of the user, allergies of the user, surgical history, past medical screenings and procedures, past hospitalizations and visits, social history (alcohol, tobacco, and drug use, sexual history and habits, occupation, living conditions), health maintenance information (exercise habits, diet information, sleep data, vaccination data, therapy and counseling history), health provider preferences, health benefits information, and genetic profile of the user.

Other fields within the user electronic medical record 42 are user-controlled, such that authorized persons including the patient who is the subject of the medical record can make entries in the medical record. Further, the user may adjust user settings 44 to allow the first correlator 36 to programmatically update the user-controlled fields of the user electronic medical record 42 with either inferred data in user profile 32 derived from user data 26 or personal history 30 that is correlated with corresponding geolocation data. In this way the electronic medical record 42 may be programmatically updated to include medical device data such as inhaler usage, blood sugar monitoring levels, insulin pump usage, etc., and biometric data such as heart rate and blood pressure history, sleep history, body temperature, galvanic skin response, etc.

A second correlator 50 is configured to correlate a plurality of medical data from electronic medical records 42 from a plurality of users with corresponding geolocation data to form a second aggregated time and location-based history 54 based on the stored user electronic medical records of an entire user population or a predefined cohort thereof, and store the second aggregated history 54 in a mass storage device of the server system 14. In this manner, statistics may be stored for all manner of user populations. For example, a percentage of the population who live within a defined geographical region and who have been diagnosed with a certain medical condition (such as H1N1 influenza) may be identified, and data about this subset of persons may be compared to identify risk factors.

A history combiner 41 is configured to combine the first aggregated time and location-based history 38 with the second aggregated time and location-based history 54 and generate a global aggregated time and location-based history that includes time and location-based history that was correlated by the first correlator 36 and the second correlator 50, and subsequently anonymize the global aggregated time and location-based history so as to form combined time and location-based data. Accordingly, every piece of medical and non-medical information from the user electronic medical record 42, client computing devices 12, medical devices 22, and other client computing devices 16 is assigned a time and location and consolidated into one comprehensive, anonymized data set organized by time and location in chronological order, allowing for easy and convenient spatial and temporal analysis of health information that a health recommender uses to make useful recommendations as well as visualize comprehensive health information for users.

Third party medical information sources 58 from third party alert sources 62 also input alerts 60, medical information 56 into the second aggregated history 54. Examples of medical information 56 includes current practices and procedures, differential diagnostic information that medical professionals use to distinguish between possible diagnoses for a given set of symptoms, descriptions of medical conditions including diseases and syndromes, and their associated symptoms, information on standardized medical screenings recommended by age and gender of the patient, information on standardized vaccination schedules recommended for children and adults, medical conditions associated with certain genetic profiles, drug information such as doses, allergens, potential interactions, etc. Examples of third party medical sources 58 include medical publishers, professional medical organizations. Examples of alerts 60 include reports from governmental and non-governmental organizations that report the occurrence of disease in particular geographic regions, including the boundaries of the geographic region, the type of disease reported, the number of persons affected, the mortality statistics associated with the affected persons, information about the incubation period and period of contagiousness for the disease, and any travel restrictions or recommended restrictions to the affected geographic region, etc. These alerts may be from a country's center for disease control, state or county health department, a company, a school district, a hospital, etc. It will be appreciated that the alerts 60 and medical information 56 are also associated with time-stamped geolocation data.

Figure 3:
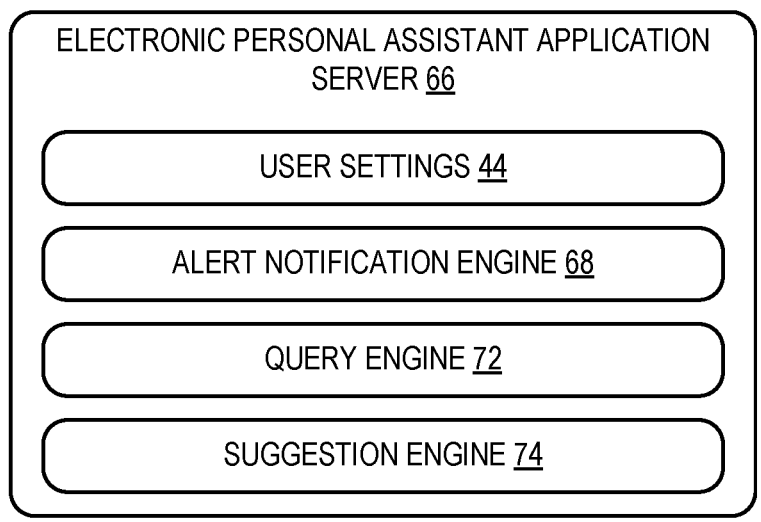
FIG. 3 shows an electronic personal assistant application server according to an embodiment of the present description.

Referring to FIGS. 1 and 3, alerts 60 from third party alert sources 62 may also be received by notification agents 64 within server system 14, which in turn instruct an alert notification engine 68 of the electronic personal assistant application server 66 to send a message 70 in the form of a push notification featuring the content of the alert 60 to the electronic personal assistant application program 24 executed on the client device 12, or multiple client devices running the personal assistant application program. In one specific example, the alert may be sent only to users who have recently traveled to the affected area, or who the data interpretation engine 28 infers will soon travel to the affected area, to inform the person of a disease outbreak in the particular geographic area. In another example, the alert may be sent to only to persons who have been detected by the system as being within a threshold distance of a person who has been diagnosed with a contagious disease throughout the period which the diagnosed person was contagious. Such a notification can be made while maintaining the privacy of the diagnosed individual.

Referring to FIGS. 1 and 3, in addition to push notifications for alerts 60, electronic personal assistant application server 66 also includes a query engine 72 configured to respond with messages 70 in the form of replies to a user query 76 received from the electronic personal assistant application program, and a suggestion engine 74 configured to proactively send messages 70 in the form of suggestions to the electronic personal assistant application programs based on user settings 44 and a set of programmatic suggestion rules. In one specific example, the client computing device 12 may display a query interface, such as a text box or voice prompt, and the user may type in a query or speak a query to the client computing device, such as "What could be causing this headache?" This user query 76 is sent to the query engine 72, which performs searches in each of the databases 30, 38, 42, and 52, subject user authorizations via settings 44 to conduct searches using each of these databases. Results are returned from each database relating to causes for headaches. The user profile may indicate that the user is a "coffee drinker," and the purchase history and location history may indicate the user visits coffee shops on average 2-3 times a day but has not visited a coffee shop in the past 2 days. The first aggregated history may indicate that "coffee drinkers" report having headaches more often than the general population. The user electronic medical record 42 may include a prior doctor visit in which the complained of a headache after suffering from heatstroke. The second aggregated history 54 may contain medical information 56 that indicates that heatstroke is typically experienced when a user sweats profusely in extremely hot temperatures and experiences fast heartbeat. The user data 26 may show extremely hot ambient temperatures but may not show galvanic skin response indicative of sweating nor a pulse indicative of fast heartbeat. In this case the query engine would apply weightings that result in ranking the possible causes of the headache as (1) caffeine withdrawal, and (2) heat exhaustion, and display this information to the user with a recommendation to seek the advice of a health care professional.

Referring to FIGS. 1 and 3, the electronic personal assistant application program 24 may solicit user feedback 78 from the user regarding the effectiveness or appropriateness of the message 70, which may in turn be transmitted back to the electronic personal assistant application server 66, and used by machine learning algorithms executed thereon to continually improve the weightings and logic by which the electronic personal assistant application server 66 makes decisions regarding the content to send to the client computing device in message 70. Continuing with the above example, if the user's headache was in fact caused by caffeine withdrawal, as diagnosed during a visit to a healthcare professional, the user might enter feedback indicating the first displayed search result was correct, and that information could then be passed to the query engine 72 as a confirmed result for machine learning algorithms that strengthen the weightings upon which the ranking was based when such confirmations are received.

In certain embodiments of the claimed invention, the computing system 10 may be further configured to determine and output health recommendations for a patient or user. It will be understood that the user population comprises patients and potential patients in an inpatient or outpatient setting. For the purposes of this description, patients will be considered synonymous with users. The client computing device may send user data 26 that include the patient's signs and symptoms. For example, a user may dictate various symptoms into the client computing device ("pain", "shortness of breath", "dry cough", "fatigue", etc.). A user may qualify symptoms by describing them further. For example, the user may qualify pain by describing the onset, precipitating factors, quality, radiation, severity, temporal factors, acuity and severity, associated symptoms, exacerbating factors, and relieving factors. The user may also input signs in various ways. One way is to dictate the signs as the user has measured them (dictating body temperature, body weight, blood glucose levels, pulse oximetry, blood pressure). A user may also take a picture of a skin lesion for later identification. Medical devices 22, such as blood glucose monitors, inhalers, respirators, may be wirelessly connected to the client computing device so that data that is collected on these devices may be seamlessly transferred to the client computing device 12 for subsequent transmission to the personal assistant user data interpretation engine 28. In more advanced applications, biochemical test devices including FISH may be used to collect real-time gene expression profiles for users.

The interpretation engine 28 may then subsequently synthesize the various pieces of data collected as described above, drawing inferences as to their relevance for the purpose of providing health recommendations. The interpretation engine 28 is configured to parse the user data 26 to organize and structure them into medically relevant information that can then be used as a basis for adding to the user personal history 30 for subsequently making health recommendations. The user personal history 30 comprises a body of various user data 26 that is personally specific to the user, which may include medically relevant information.

The combined time and location-based data, formed by the history combiner 41, may include medically relevant information about multiple users, so that the data may become the subject of epidemiological studies such as disease etiology, biomonitoring, and outbreak investigation. Specific users may be grouped into specific populations for clinical trials and cohort studies, for example. The personal assistant application server 66 may analyze patterns and trends in the first aggregated history 38, second aggregated history 54, and the combined time and location-based data to draw conclusions about the patterns, causes, and effects of the various signs and symptoms to inform the health recommendations for the user. These inferred patterns and trends may even be communicated to trusted health partners and agencies, such as the CDC and other governmental health agencies, for example.

The electronic personal assistant application server 66 may receive the user electronic medical record 42, user personal history 30, and combined time and location-based data to retrieve key pieces of personal medical information that may be helpful in inferring the significance of the patient's signs and symptoms. These include past medical history, medications, past hospitalizations, family history, social history, occupational history, and environmental history. For example if a patient asthma reports shortness of breath on the client computing device, the application server 66 may evaluate the combined time and location-based data and correctly correlate the symptom with the patient's asthma and recent environmental history that may reveal possible triggers that caused the symptoms. The application server 66 may also associate certain symptoms with a time point at which the patient started a medication and infer an adverse effect of the medication, for example. It will be appreciated that the information and data that is received or retrieved by the electronic personal assistant application server 66 are subsequently sent to the electronic personal assistant application program 24 and the health recommender 25.

Figure 2:
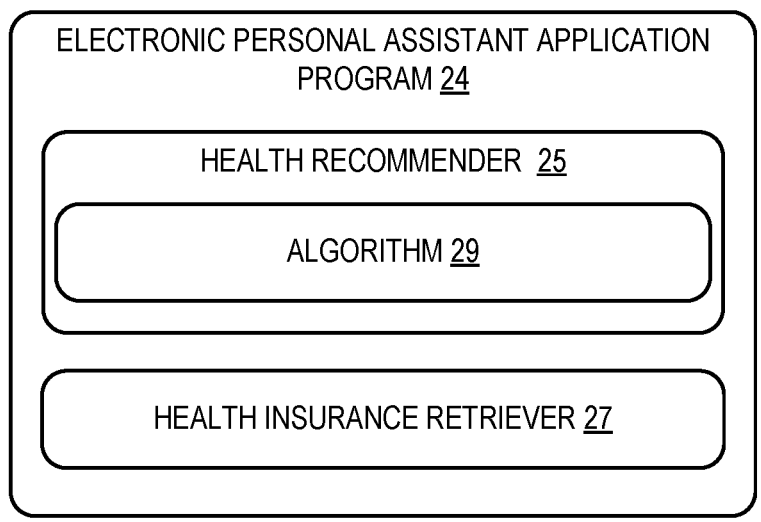
FIG. 2 shows an electronic personal assistant application program according to an embodiment of the present description.

Referring to FIG. 2, the personal assistant application program 24 may further include a health recommender 25, which is configured to identify at least one health condition of the user, determine a health recommendation that is based at least on the combined time and location based data, a user's health insurance information, user electronic medical record 42, the identified health condition, and output the health recommendation to a display associated with the computing device. The health recommender 25 is instantiated in the application 24 in the client computing device 12 and communicates with the electronic personal assistant application server 66, which receives the user personal history 30, user electronic medical record 42, and combined time and location-data including the first aggregated history 38 and the second aggregated history 54. Based upon the above inputs, which may also comprise user input from the user, a healthcare provider that reported the signs, a search query entered by the user, a browsing history of the user, and/or sensor data received from a sensor associated with the computing device 12, the health recommender 25 may identify the health condition. The health recommender 25 may determine a health recommendation implementing a machine-learning algorithm 29 that iteratively processes at least one of signs, symptoms, health records, genomic data, online behavior data, search queries, location data, user feedback, health insurance information, and context information of one or more users to inform and modify the algorithm over time. It will be appreciated that the inputs of the health recommender 25 are not limited to the above, and may encompass other inputs that are relevant to determining a user's health recommendations.

The combined time and location-data with anonymized medical and non-medical data may be outputted to a display associated with the computing device to inform the user about the evidence that was used to determine the user's health recommendations. For example, a low rate of vaccinations in a user's neighborhood may be represented by a map showing the high number of unvaccinated residents in the vicinity, overlaid by a graphical representation of reported flu symptoms in the same vicinity. Accordingly, the health recommender may recommend precautions for children, pregnant women, and immunocompromised patients who might enter the user's neighborhood, informed not only by medical and non-medical data from client computing devices, but also from the electronic medical records as well. The outputted combined time and location-data may be saved as an image that can be shared with others on a network, printed, or otherwise exported to other applications.

Implementing a Bayesian machine-learning algorithm 29, the health recommender 25 may incorporate a differential diagnosis engine for associating signs and symptoms to determine a health recommendation that is based at least on the user's health insurance information, the user's electronic medical record, the identified health condition, and the combined time and location-based data. The health recommender 25 may provide a list of differential diagnoses in the order of likelihood, taking into account the patient's personal medical information as well as the first aggregated history 38 from multiple users. For example, when an analysis of the first aggregated history 38 reveals that a cluster of individuals in a certain geographic area has reported symptoms of fever and chills, cough, headache, and sore throat, the algorithm 29 may be able to recognize that the patient is one of those affected by the regional flu epidemic. The health recommender 25 may also output the combined time and location-data to a display as a graphical map showing reported flu symptoms and diagnosed cases of influenza in a certain geographic area.

As another example, a plurality of measurements of air pollen and pollutant concentrations with time-stamped geolocation data may be received from a plurality of client computing devices 12 and official monitoring devices that comprise third party medical information sources 58. The first correlator 36 correlates a plurality of reports of respiratory symptoms (shortness of breath, coughing, wheezing), medical device data showing increased use of respiratory medications among a subset of the users, and air pollen and pollutant concentrations measurements from a plurality of client computing devices 12 with corresponding time-stamped geolocation data to generate a first aggregated time and location-based history. The second correlator 50 correlates a plurality of electronic medical records and official air concentration measurements from official monitoring devices with corresponding time-stamped geolocation data, generating a second aggregated time and location-based history, identifying currently diagnosed asthma and obstructive disease patients among the users. The history combiner 41 combines the first aggregated history with the second aggregated history to generate a global aggregated history, which is subsequently anonymized so as to form combined time and location-based data. The health recommender 25 may identify the worsening asthma of the user, identify health recommendations based on the combined data (which may show increased air pollutant concentrations and other affected users in the vicinity), health insurance information, the user electronic medical record, the identified worsening asthma, and output the health recommendations (stay indoors, use supplemental oxygen, use indoor air filter, increase nebulizer use, for example). The health recommender 25 may also display the combined time and location-based data as an interactive map showing the temporal and geographic distribution of respiratory symptoms, air pollen and pollutant concentrations, the respiratory symptoms of a subset of users (asthma and/or obstructive disease patients, patients with specific allergies), and respiratory medication use.

The algorithm 29 may also classify the patient's signs and symptoms into tiers according to acuity and severity, so that the patient may be directed to the appropriate healthcare professionals. For example, the health recommender 25 may advise a patient with a mild, self-limiting headache to try an NSAID medication at home. An asthma patient whose inhalers are losing their effectiveness may be asked to schedule an appointment with a doctor. On the other hand, a heart failure patient with acutely worsening shortness of breath would be asked to visit the ER immediately. It will be appreciated that the health recommender 25 will receive a user's health insurance information that is retrieved by the health insurance retriever 27 and make referrals to healthcare providers and medical services based upon the specific health insurance and individual preferences of the user. For example, the health recommender 25 may apply search filters to narrow the list of recommended specialists to in-network healthcare providers, hospitals, and clinics. When a user is presented with a narrowed list that has certain results excluded because they are not covered by user's health insurance, a selector may be provided for the user to view excluded results as well, in case the user desires to see the full results, including both in-network and out-of-network results. The user may adjust individual preferences in the user settings 44 to include or exclude certain services that the health recommender 25 may recommend, such as alternative medicine clinics and chiropractic treatment centers. The user may further adjust individual preferences to include or exclude medical services that the health recommender 25 may recommend based upon financial factors, including deductibles, out-of-pocket expenses, and copayments.

Further, instead of passively waiting for users to qualify their presenting signs and symptoms, the health recommender 25 may also actively present a series of health related questions to the user to retrieve more history of the present illness, including a review of systems. It will be understood that this is not to replace the healthcare professional's role in properly diagnosing patients in the clinical setting. Rather, the purpose is to triage patients to help properly direct them to the proper medical services that are available to them, as well as document signs and symptoms that may be useful to review and evaluate by the patients' primary care providers. Thus, the series of health questions may be revised and updated by a healthcare provider accordingly to the most current, up-to-date guidelines, protocols, and standards of care. Once user responses are received, the health recommender 25 may send the user responses to a recommended healthcare provider.

The documentation of data by the health recommender 25 may not be limited to signs and symptoms dictated by the user, and may also include signs and/or symptoms that are identified by a search query 76 entered by the user, and browsing history of the user. For example, in addition to noting the shortness of breath and inhaler uses of the asthma patient, the health recommender 25 may also note that the user has queried asthma attacks on the search engine. The health recommender 25 may interpret this browsing history as a cue to prioritize asthma in its health recommendations. Further, at least the timing of the user's search query may be used to determine the acuity and severity of the signs and/or symptoms. For example, the health recommender 25 may infer that an elderly patient who searches "dark stools" following bowel surgery may have some residual gastrointestinal bleeding that may need to be closely monitored and documented for later review.

With further reference to FIGS. 2 and 3, the personal assistant application program may further include a health insurance retriever 27 configured to retrieve health insurance information from a health insurance server. The health insurance server may be components that store the health insurance information, which may be at a user electronic medical record 42 or user personal history 30. The health insurance retriever 27 may retrieve health insurance information by performing a query on a query engine 72 that is instantiated on the electronic personal assistant application server 66. The health insurance information may include details such as the health insurance plan that currently covers the patient, the healthcare services and network providers that are currently available to the patient under the user's health insurance, the health management organizations (HMO), exclusive provider organizations (EPO), and preferred provider organizations (PPO) that the patient belongs to, and prescription and non-prescription drug plans for the patient. The health insurance information may draw from other information sources and include such pieces of data as the geographic location of the user, third party reviews of providers, a user's personal calendar, and the user's demographic information, including preferred languages. It will be understood that the health insurance information that is selected to be accessed will be relevant to the signs and/or symptoms that are identified by the health recommender 25, and appropriate to be used to make health recommendations for the patient.

The computing system 10 is configured to be HIPAA compliant to maintain the privacy and security of individually identifiable health information. Accordingly, the electronic application server 66 may include customizable user settings to change privacy settings and actively control the amount of personal information that may be accessible to the interpretation engine 28, personal assistant application server 66, or any other component of the computing system 10. It will be appreciated that digital precautions, including encryption, will be implemented for such personal information as electronic medical records 42 and user personal history 30 to protect against identity theft and multiple levels of permissions would be required to access sensitive information.

Figure 4:
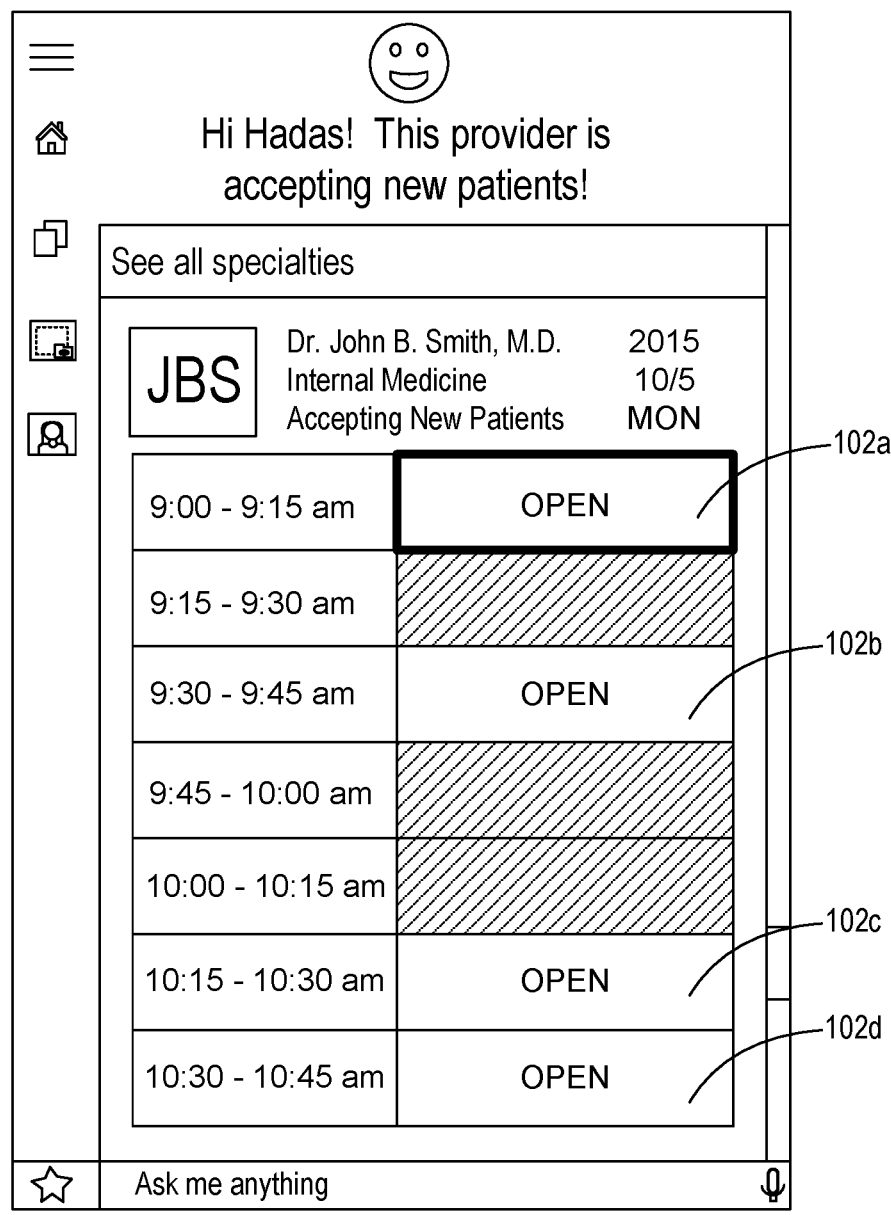

Referring to FIG. 4, to further assist patients in seeking proper medical attention, the health recommender 25 may be configured to display on the computing device an appointment scheduling interface 100 with available timeslots 102a, 102b, 102c, and 102d at a recommended healthcare provider, receive a user selection of a selected timeslot 102a, and transmit the user selected timeslot and user ID of the user to the healthcare provider to make an appointment. For example, if the health recommender 25 recommends visiting the ER, the computing device 12 may be configured to dial 911. In other situations, if the health recommender 25 recommends scheduling an appointment with the primary care physician, the interface may direct the user to the patient's preferred primary care provider on the patient's network provider or HMO to conveniently schedule an appointment.

Referring to FIG. 5, following an appointment, the health recommender 25 may be configured to display on the computing device a follow up message 104 to the user, in which the user is asked to provide user feedback. This may be in form of a survey with multiple choice options with qualitative and quantitative assessments to evaluate the user's satisfaction and quality of user experience, as well as indicate to the personal assistant application how relevant and helpful the health recommendations were.

Figure 6:
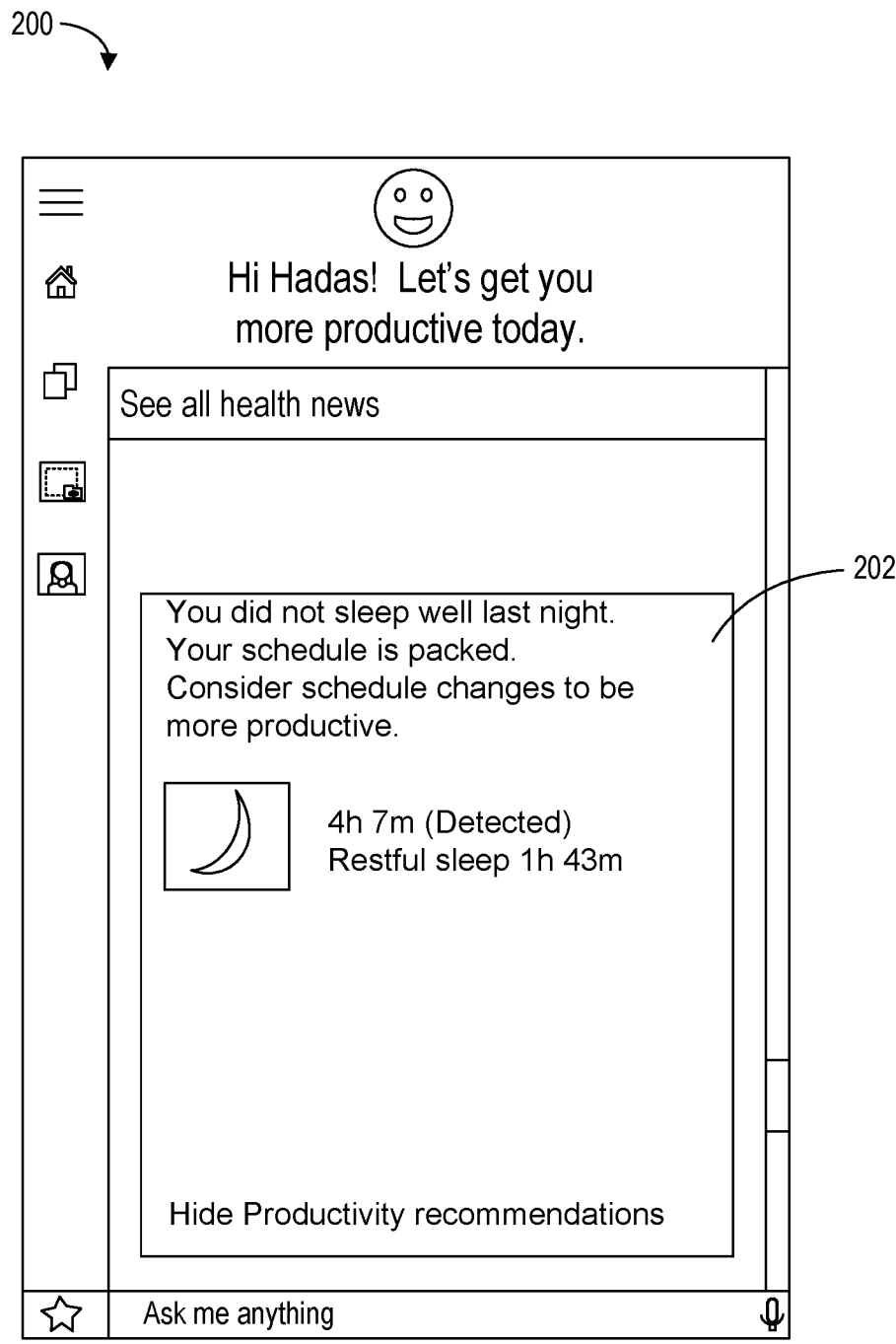
FIGS. 6 and 7 show an example recommendation interface according to an embodiment of the present description.
Figure 7:
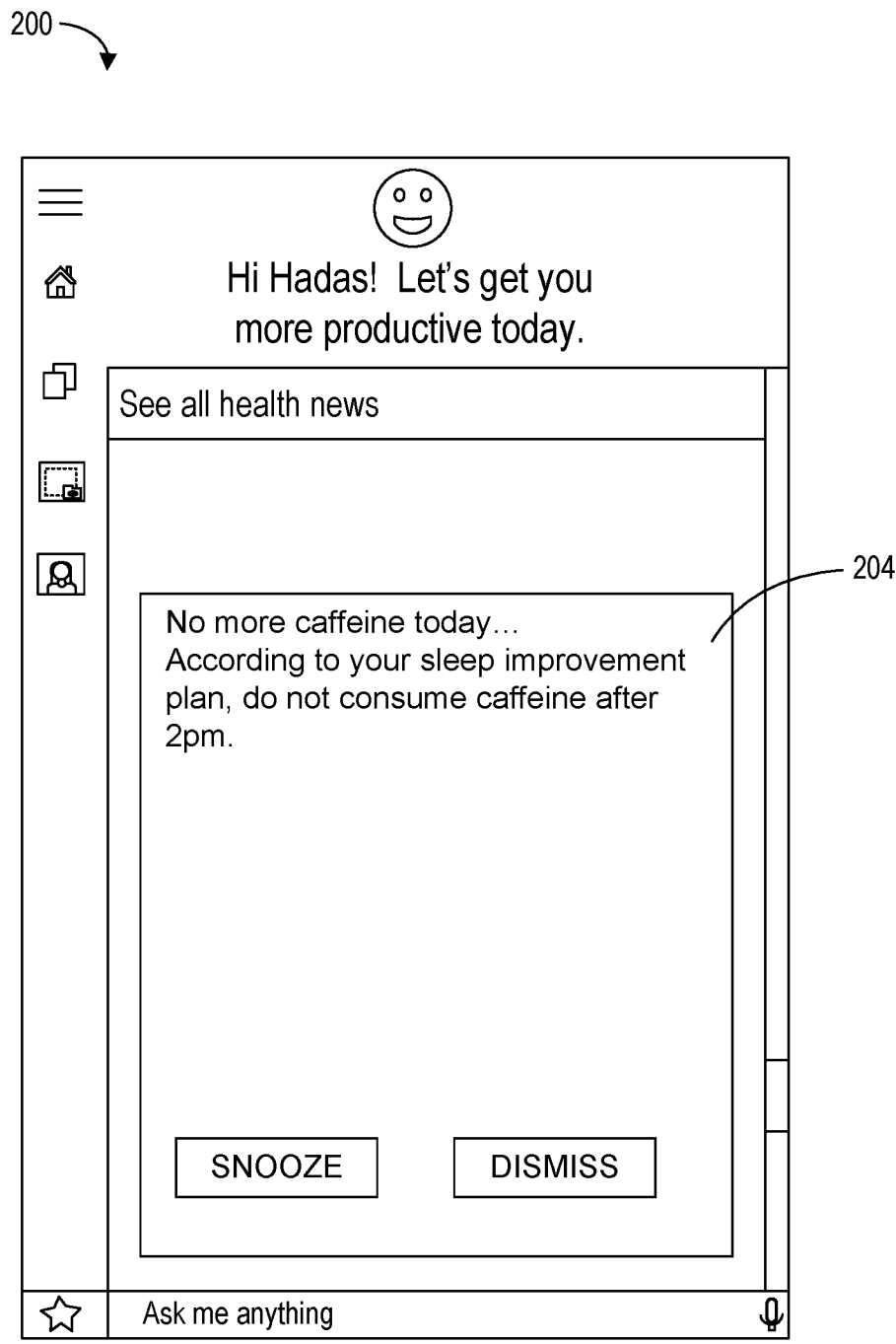

Referring to FIG. 6, one possible implementation of the health recommender 25 is illustrated for a patient with trouble sleeping. In this example, the health recommender 25 is configured to display on the computing device 12 an interface 200 for making health recommendations. A biometric sleep sensor, which is a wearable computing device 18, detects 4 hours and 7 minutes of sleep and only 1 hour and 43 minutes of restful sleep from a patient suffering from insomnia. The user data 26 containing the biometric sleep data is sent to the interpretation engine 28, which interprets the biometric data and parses it into sleep data that is transmitted and stored in the user personal history 30. The health recommender 25 identifies the signs of insomnia from the sleep data that is retrieved from the user personal history 30. The machine-learning algorithm 29 implemented by the health recommender 25 is configured to process a variety of data from various sources, including other signs and symptoms reported by the user, health records, online behavior data, location data, and context information to determine a health recommendation 202. In this example, based on context information, the health recommender 25 notes that the user is maintaining a busy schedule that may be contributing to a lack of sleep, and the health recommender 25 makes a recommendation to consider schedule changes. The recommendations may be also be structured as a holistic lifestyle plan that is ongoing—as illustrated in FIG. 7, the health recommender 25 may formulate a sleep improvement plan for an insomnia patient and issue a recommendation 204 to discourage caffeine consumption as part of the plan. The recommendation 204 may be formulated according to a user's health insurance information that is retrieved by the health insurance retriever 12, especially if the HMO or network provider of the user endorses specific preventative lifestyle programs that promote healthy lifestyle changes that encompass occupational safety, sleep habits, diet, and exercise.

In some embodiments, the methods and processes described herein may be tied to a computing system of one or more computing devices. In particular, such methods and processes may be implemented as a computer-application program or service, an application-programming interface (API), a library, and/or other computer-program product.

Figure 8A:
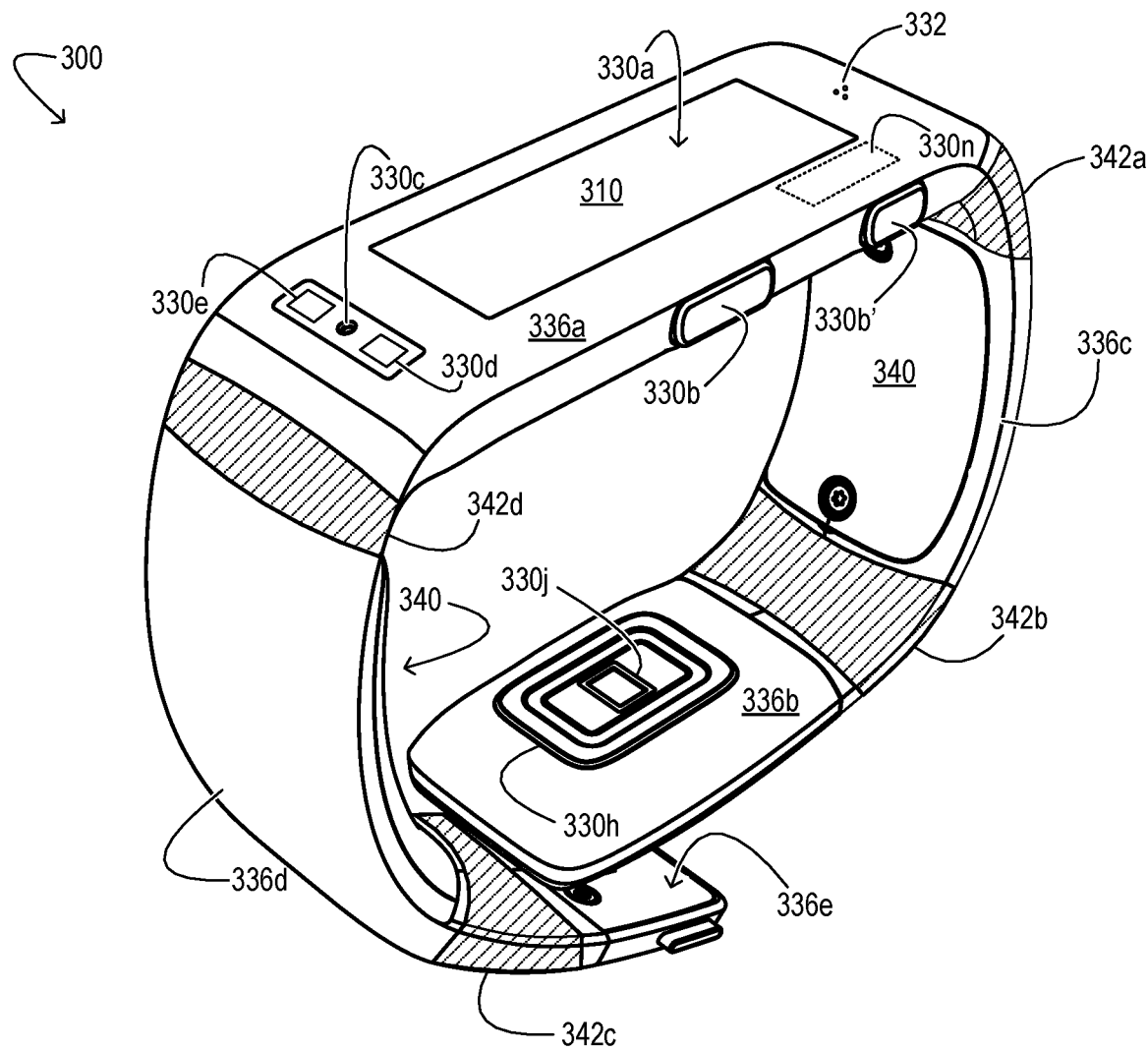
FIGS. 8A and 8B show aspects of one example of a wearable computing device according to an embodiment of the present description.
Figure 8B:
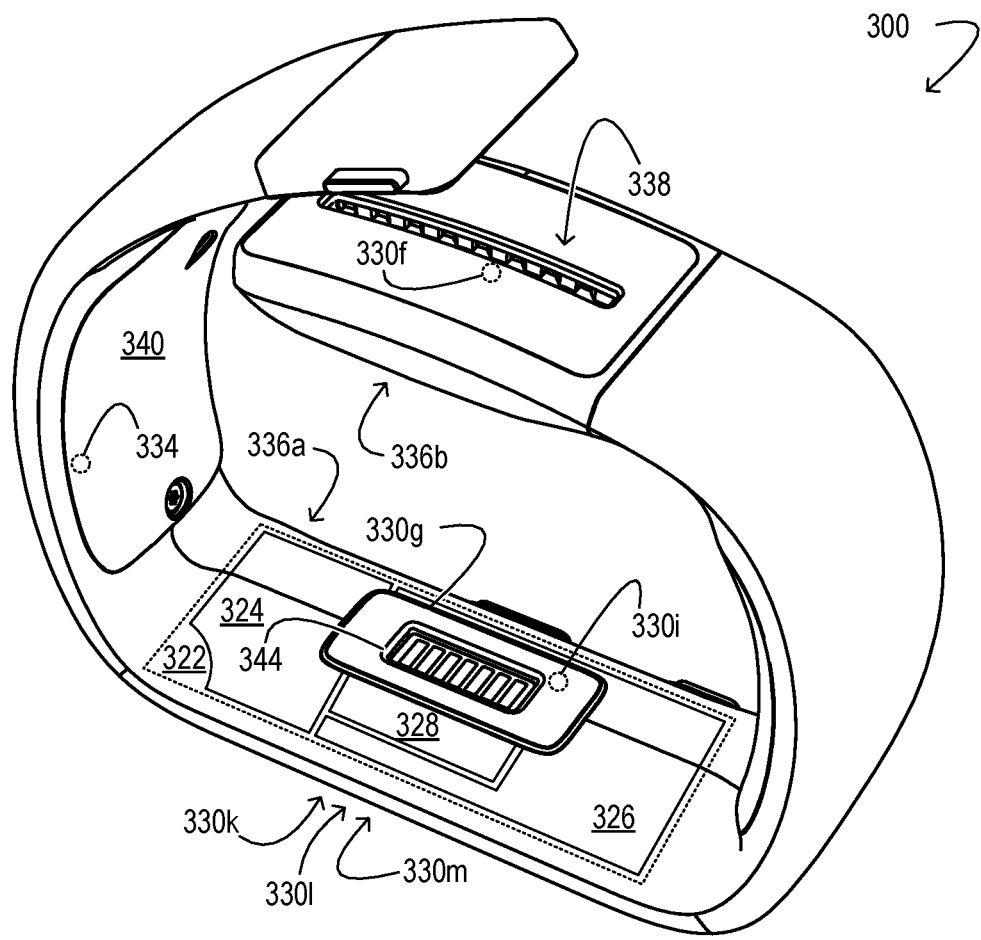

Referring to FIGS. 8A and 8B, one example of a wearable computing device 18 is given as a composite band 300. In composite band 300, touch-screen sensor 330A is coupled to display 310 and configured to receive touch input from the wearer. In general, the touch sensor may be resistive, capacitive, or optically based. Push-button sensors (e.g., microswitches) may be used to detect the state of push buttons 330B and 330B', which may include rockers. Input from the push-button sensors may be used to enact a home-key or on-off feature, control audio volume, microphone, etc.

Other sensors 330 of composite band 300 include microphone 330C, visible-light sensor 330D, ultraviolet sensor 330E, and ambient-temperature sensor 330F. The microphone provides input to compute system 322 that may be used to measure the ambient sound level or receive voice commands from the wearer. Input from the visible-light sensor, ultraviolet sensor, and ambient-temperature sensor may be used to assess aspects of the wearer's environment.

FIGS. 8A and 8B further show a pair of contact sensors—charging contact sensor 330G arranged on display-carrier module 336A, and pillow contact sensor 330H arranged on pillow 336B. The contact sensors may include independent or cooperating sensor elements, to provide a plurality of sensory functions. For example, the contact sensors may provide an electrical resistance and/or capacitance sensory function responsive to the electrical resistance and/or capacitance of the wearer's skin. To this end, the two contact sensors may be configured as a galvanic skin-response sensor, for example. In the illustrated configuration, the separation between the two contact sensors provides a relatively long electrical path length, for more accurate measurement of skin resistance. In some examples, a contact sensor may also provide measurement of the wearer's skin temperature. In the illustrated configuration, a skin temperature sensor 330I in the form a thermistor is integrated into charging contact sensor 330G, which provides direct thermal conductive path to the skin Output from ambient-temperature sensor 330F and skin temperature sensor 330I may be applied differentially to estimate of the heat flux from the wearer's body. This metric can be used to improve the accuracy of pedometer-based calorie counting, for example. In addition to the contact-based skin sensors described above, various types of non-contact skin sensors may also be included.

Arranged inside pillow contact sensor 330H in the illustrated configuration is an optical pulse-rate sensor 330J. The optical pulse-rate sensor may include a narrow-band (e.g., green) LED emitter and matched photodiode to detect pulsating blood flow through the capillaries of the skin, and thereby provide a measurement of the wearer's pulse rate. In some implementations, the optical pulse-rate sensor may also be configured to sense the wearer's blood pressure. In the illustrated configuration, optical pulse-rate sensor 330J and display 310 are arranged on opposite sides of the device as worn. The pulse-rate sensor alternatively could be positioned directly behind the display for ease of engineering.

Composite band 300 may also include inertial motion sensing componentry, such as an accelerometer 330K, gyroscope 330L, and magnetometer 330M. The accelerometer and gyroscope may furnish inertial data along three orthogonal axes as well as rotational data about the three axes, for a combined six degrees of freedom. This sensory data can be used to provide a pedometer/calorie-counting function, for example. Data from the accelerometer and gyroscope may be combined with geomagnetic data from the magnetometer to further define the inertial and rotational data in terms of geographic orientation.

Composite band 300 may also include a global positioning system (GPS) receiver 330N for determining the wearer's geographic location and/or velocity. In some configurations, the antenna of the GPS receiver may be relatively flexible and extend into flexible segment 342A.

Figure 9:
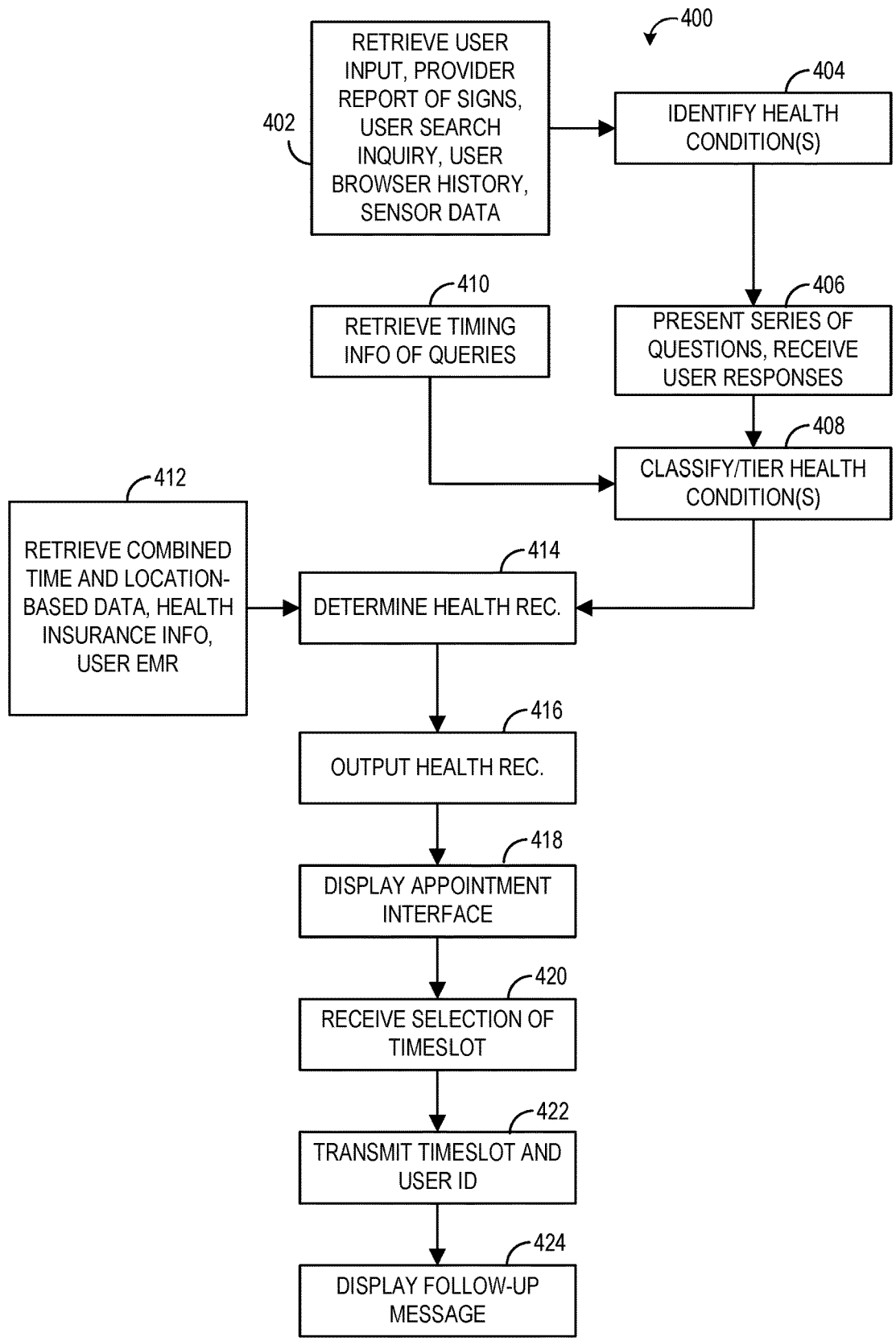
FIG. 9 shows an example computer method according to one embodiment of the present description.

FIG. 9 illustrates an example of a method 400 for determining and outputting health recommendations for a user. At 402, the method 400 includes retrieving user input from the user, a healthcare provider reporting the sign, a search query entered by the user, a browsing history of the user, and/or sensor data received from a sensor associated with the computing device. At 404, the method includes identifying at least one health condition of the user based upon the retrieving user input from the user, a healthcare provider reporting the sign, a search query entered by the user, a browsing history of the user, and/or sensor data received from a sensor associated with the computing device. At 406, the method 400 may further include presenting a series of health related questions to the user and receiving user responses to the questions. Optionally, the user responses may then be sent to a recommended healthcare provider; the series of health related questions may be revised and updated by a healthcare provider. At 408, the method 400 may further include classifying the health condition into a tier according to acuity and severity. At 410, the method may further include determining the acuity and severity of the health condition based at least on a timing of the user's search query, where the health condition is identified by a search query entered by the user.

At 412, the method 400 includes retrieving combined time and location-based data from aggregated histories of a plurality of users, the user electronic medical record, and identified health condition, which inform a machine-learning algorithm that is implemented by a health recommender. At 414, the method 400 includes determining a health recommendation at least based on the combined data, the user electronic medical record, and the identified health condition. The health recommendation may include at least a referral to a healthcare provider and/or medical service based at least on the health insurance information and the user's preferences. At 416, the method 400 includes outputting the health recommendation to a display associated with the computing device. At 418, the method 400 includes display on the computing device an appointment scheduling interface with available timeslots at a recommended healthcare provider. At 420, the method 400 includes receiving a user selection of a selected timeslot. At 422, the method 400 includes transmitting the user selected timeslot and user ID of the user to the healthcare provider to make an appointment. At 424, the method 400 includes displaying on the computing device a follow up message to the user after the appointment, in which the user is asked to provide user feedback.

Figure 10:
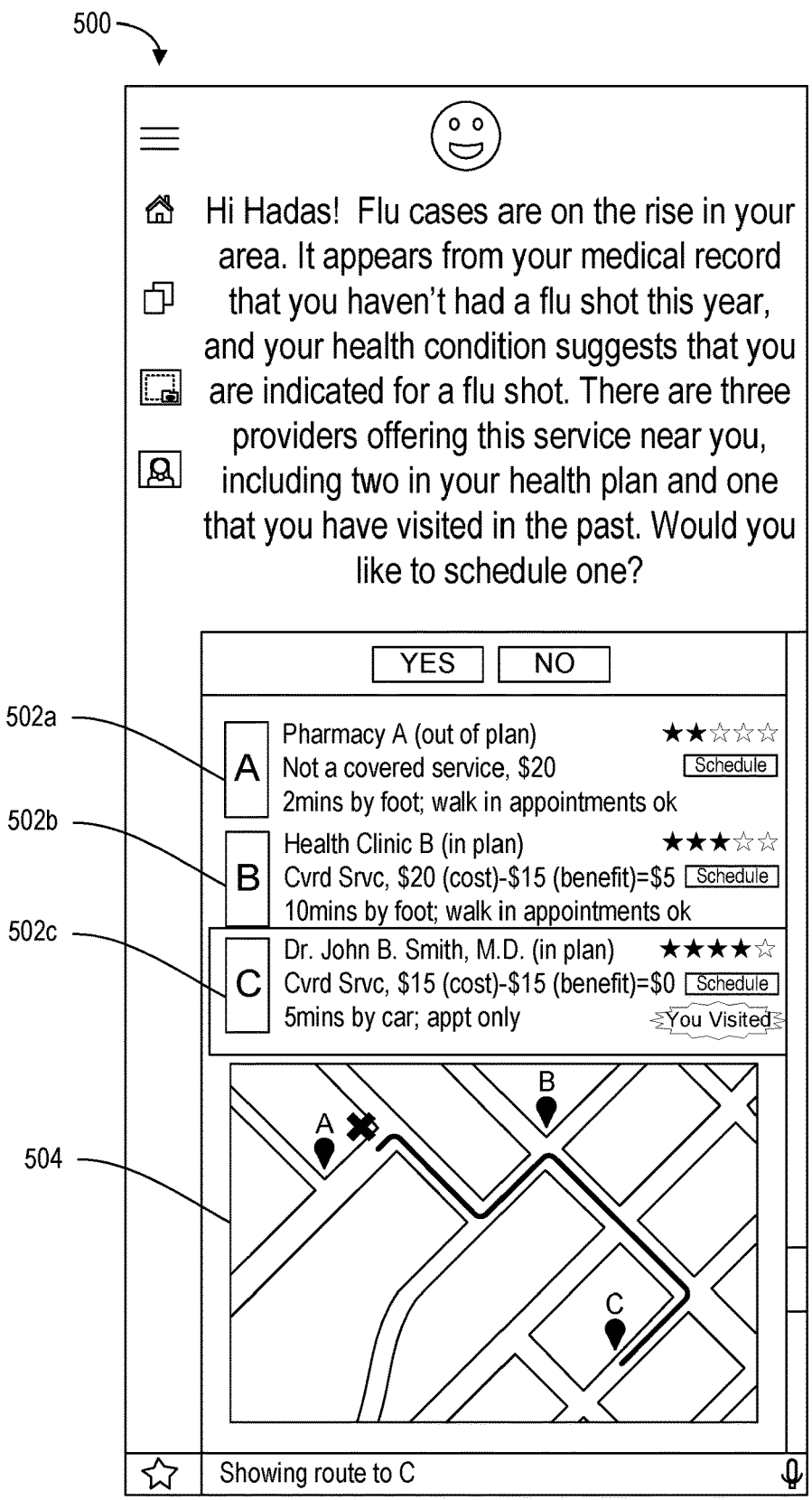
FIG. 10 shows an example recommendation interface according to another embodiment of the present description.

Referring to FIG. 10, another possible implementation of the health recommender 25 is illustrated for a user who has not had a flu shot in the past year. In this example, the health recommender 25 is operatively coupled to a display and a health insurance retriever 27. The health recommender 25 determines a health recommendation based on the user's vaccination history (in this example, indicating that the user has not received a flu shot in the past year) which is included in the combined time and location-based data from the history combiner 41 and the electronic medical records 42 that were correlated by the second correlator 50. The health recommender 25 may also determine the health recommendation by identifying at least a health condition of a plurality of users in the vicinity of the user based on the combined time and location-based data (in this example, identifying a rise in flu cases in the user's vicinity), using the ability to access user data from multiple users to rapidly conduct epidemiological analyses to identify disease clusters as they develop in real-time, better informing the user and the health recommendations that are tailored for the individual user. The health recommender 25 identifies a health condition (such as the presence or absence of signs, symptoms, complaints, etc.) from the user data 26 that the user reports using the client computing device 12. In the depicted embodiment, the user's determined health condition is an absence of an acute, moderate to severe illness for which medical caution may be advised prior to administering the flu shot. Accordingly, the health recommender 25 determines a health recommendation, stating that the user has an indication for a flu shot. Alternatively, the health recommender 25 may also identify a health condition from the user personal history 30, user electronic medical record 42, and the combined time and location-data including the first aggregated history 38 and second aggregated history 54, so that the health recommender 25 may identify a presence or absence of other conditions that are pertinent to the administration of the flu shot, such as Guillain-Barré syndrome, immunocompromised states, and hypersensitivities.

Although the example in FIG. 10 is directed to a preventative vaccination, it will be appreciated that other preventative health services may be included in this embodiment. For instance, the health recommender 25 may make a health recommendation for a 51 year old woman to undergo biennial screening mammography, based on the user's profile and screening history, which are included in the combined time and location-based data from the history combiner 41 and the electronic medical records 42 that were correlated by the second correlator 50. Thus, it will be appreciated that an identified health condition could be any piece of data from the user personal history 30, user electronic medical record 42, and the combined time and location-data including the first aggregated history 38 and second aggregated history 54, that is pertinent to making a health recommendation, including gender and age. The recommendations would be based on a third party medical information source 58 such as the US Preventative Services Task Force (USPSTF), which currently recommends biennial screening mammography for women 50 to 74 years old.

The health recommendations for preventive services from the health recommender 25 may also be based on the user's geolocation data, user's genetic background, and the user's health indices. For example, if the health recommender 25 identifies that the user is a 50 year old male patient living in the US, the health recommender would recommend undergoing colorectal cancer screening, since the USPSTF currently recommends screening for colorectal cancer beginning at age 50 years and continuing until age 75 years. In another example, if the health recommender identifies that the user is a 41 year old male patient living in Japan, the health recommender would recommend undergoing colorectal cancer screening, since the Japan Cancer Society currently recommends annual screening for colorectal cancer beginning at 40 years. In an example relating to the user's genetic background, if the health recommender 25 identifies that the user is a 35 year old female patient with a family history of breast cancer, the health recommender 25 would recommend BRCA testing and earlier screening mammography based on USPSTF guidelines. In an example relating to a user's health indices, if the health recommender 25 identifies that the user's body mass index (BMB is 31 kg/m², the health recommender 25 would recommend that the user see a clinician to receive behavioral interventions, based on current USPSTF guidelines that define overweight as 30 kg/m² or higher.

Based at least on the identified health condition, the user's electronic medical record 42, and the user's geolocation data, the health recommender 25 determines a health recommendation, including at least a recommended health service. In this example, the health recommender recommends a flu shot and identifies a plurality of health care providers 502a, 502b, and 502c that deliver the recommended health care service in the vicinity of the user currently, or at a user's predicted location during an available timeslot in the future according to the user's calendar in a calendar program executed on the client computing device 12. The health insurance retriever 27 retrieves the user's health insurance information, which indicates whether the flu shot service (recommended health care service) is covered by the user's health insurance plan at each of the plurality of health care providers 502a, 502b, and 502c. The health recommender 25 determines whether the flu shot service (recommended health care service) is covered by the user's health insurance plan at each of the plurality of health care providers 502a, 502b, and 502c, and then outputs on the display associated with the client computing device 12 a graphical representation of the health recommendation, the plurality of health care providers 502a, 502b, and 502c, and an indication of whether the recommended health care service is covered by the user's health insurance plan at each of the plurality of health care providers. In this example, the covered services are indicated by the phrase "Cvrd Srvc", while the service that is not covered is indicated by the phrase "Not a covered service." This graphical representation may include a map 504 indicating the location of the plurality of health care providers 502a, 502b, and 502c, and a route to at least one of the health care providers. The travel distance to each of the plurality of health care providers may also be displayed (for example, "2 mins by foot", "5 mins by car").

The determining of whether the recommended health care service is covered by the user's health insurance plan at each of the plurality of health care providers may include determining that the recommended health care service is included in the benefits of the user's health insurance plan (in-plan), determining that the recommended health care service is excluded from the benefits (out-of-plan), or determining that the recommended health care service is partially included in the benefits (limited benefits). For example, a screening mammogram may be fully covered by a user's health insurance plan (in-plan), while an annual occult blood test for colorectal cancer may only be reimbursed by the user's health insurance plan for 80% of the cost (limited benefits). The determining of whether the recommended health care service is covered by the user's health insurance plan at each of the plurality of health care providers may also include determining restrictions and requirements that are associated with the recommended health care service at each of the plurality of health care providers. For example, a flu shot may be associated with age restrictions, or contraindicated for patients with certain immunodeficiency syndromes, and the health recommender may not recommend the flu shot for some elderly users depending on the age restrictions, for example.

On the display, the graphical representation may further include the in-plan/out-of-plan/partial coverage status of the recommended health care service and associated restrictions and requirements as described above. The health recommender 25 may also output on the display a graphical indication of a previous relationship that the user has had to at least one of the plurality of health care providers, particularly if the user has used other services with the health care provider in the past. In this example, the interface 500 indicates that health care provider 502c has been visited in the past. The health recommender 25 may also output cost information that is associated with the health insurance plan for the recommended health service, taking into account the health insurance information of the user. For example, the health insurance information may include a reimbursement benefit amount for the recommended health care service at each of the plurality of health care providers and further include a total cost for the recommended health care service at each of the plurality of health care providers less the reimbursement benefit amount, equaling a net cost for the user. It will be appreciated that the cost information may be calculated and outputted to take into account other variables as well: child-only coverage, out of service area coverage, coinsurance, copayments, outpatient service fees, facility fees, referral fees, out-of-pocket limits, drug and device costs, HSA eligibility, Medicare and Medicaid reimbursements, and other such factors.

Like the embodiment described in FIG. 4, the health recommender 25 may be configured to display on the computing device an appointment scheduling interface 100 with available timeslots 102a, 102b, 102c, and 102d at a recommended healthcare provider for the recommended health care service, receive a user selection of a selected timeslot 102a, and transmit the user selected timeslot and user ID of the user to the healthcare provider to make an appointment. The health recommender 25 may further determine an availability of the user to receive the recommended health care service based at least on a calendar. For example, if the health recommender 25 recommends receiving a flu shot, an appointment scheduling interface may show available timeslots for flu shots at one healthcare provider. In the illustrated example, the health recommender may be programmed to present the interface shown in FIG. 10, only when the user's calendar in the calendar program executed on the client computing device indicates that the user has availability currently to receive the recommended health care service. Alternatively, the health care recommender may search for available timeslots in the future based on the user's calendar and present a map of service locations surrounding a user's predicted future location during the available timeslot.

Figure 11:
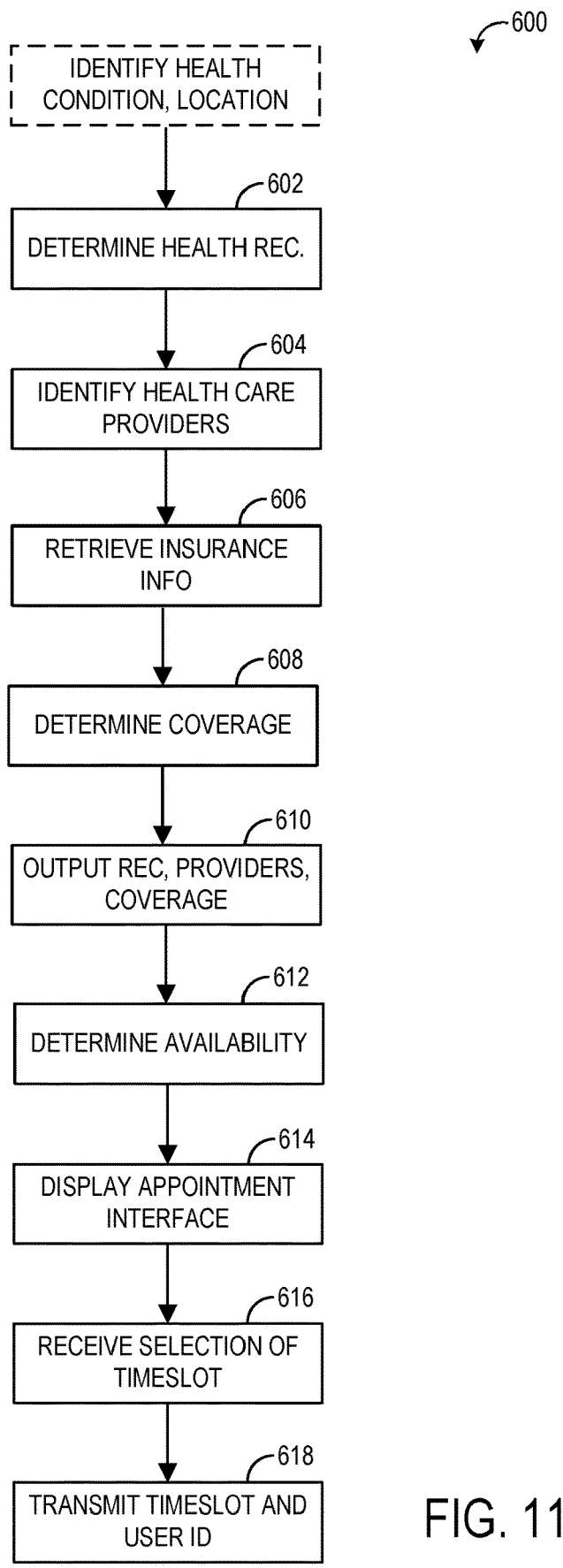
FIG. 11 shows an example computer method according to another embodiment of the present description.

FIG. 11 illustrates an example of a method 600 for determining and outputting health recommendations for a user. It will be appreciated that the method 600 is substantially similar to the method 400 in the steps leading up to step 414, which includes determining a health recommendation. Therefore, the steps that are performed before step 602, which includes determining a health recommendation, will be omitted for the sake of brevity. At 602, the method 600 includes determining a health recommendation, including at least a recommended health care service, at least based on the identified health condition, the user's electronic medical record, and the user's geolocation data. At 604, the method 600 includes identifying a plurality of health care providers that deliver the recommended health care service in a vicinity of the location of the user. At 606, the method 600 includes retrieving the user's health insurance information, indicating whether the recommended health care service is covered by the user's health insurance plan at each of the plurality of health care providers. At 608, the method 600 includes determining whether the recommended health care service is covered by the user's health insurance plan at each of the plurality of health care providers. At 610, the method 600 includes outputting on a display associated with the client computing device a graphical representation of the health recommendation, the plurality of health care providers, and an indication of whether the recommended health care service is covered by the user's health insurance plan at each of the plurality of health care providers.

At 612, the method 600 includes determining an availability of the user to receive the recommended health care service based at least on a calendar, which may be a service provider calendar or a user calendar, or both. FIG. 4 depicts one example of a service provider calendar, and use of a user calendar is also described above in relation to FIG. 10. At 614, the method 600 includes display on the computing device an appointment scheduling interface with available timeslots at a recommended healthcare provider for the recommended health care service. At 616, the method 600 includes receiving a user selection of a selected timeslot. At 618, the method 600 includes transmitting the user selected timeslot and user ID of the user to the healthcare provider to make an appointment.

Figure 12:
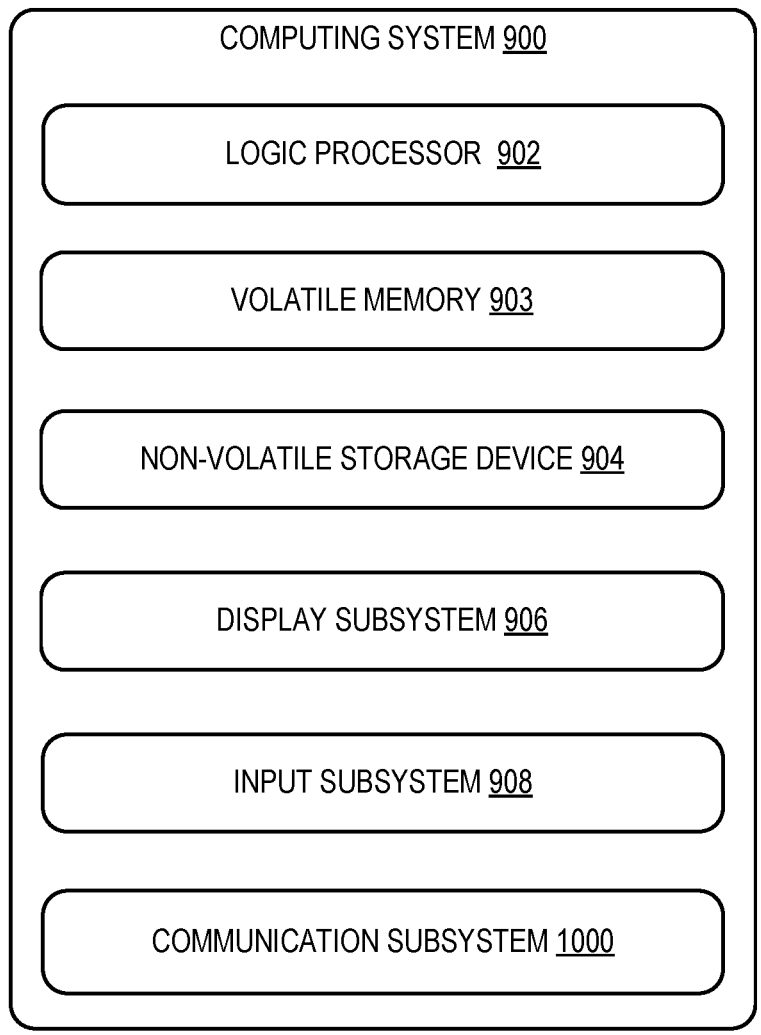
FIG. 12 shows an example computing system according to an embodiment of the present description.

FIG. 12 schematically shows a non-limiting embodiment of a computing system 900 that can enact one or more of the methods and processes described above. Computing system 900 is shown in simplified form. Computing system 900 may embody one or more of the servers or client computing devices 12 or other computing devices 16 of FIG. 1. Computing system 900 may take the form of one or more personal computers, server computers, tablet computers, home-entertainment computers, network computing devices, gaming devices, mobile computing devices, mobile communication devices (e.g., smart phone), and/or other computing devices, wearable computing devices such as smart wristwatches and head mounted augmented reality devices, computerized medical devices.

Computing system 900 includes a logic processor 902 volatile memory 903, and a non-volatile storage device 904. Computing system 900 may optionally include a display subsystem 906, input subsystem 908, communication subsystem 1000, and/or other components not shown in FIG. 10.

Logic processor 902 includes one or more physical devices configured to execute instructions. For example, the logic processor may be configured to execute instructions that are part of one or more applications, programs, routines, libraries, objects, components, data structures, or other logical constructs. Such instructions may be implemented to perform a task, implement a data type, transform the state of one or more components, achieve a technical effect, or otherwise arrive at a desired result.

The logic processor may include one or more physical processors (hardware) configured to execute software instructions. Additionally or alternatively, the logic processor may include one or more hardware logic circuits or firmware devices configured to execute hardware-implemented logic or firmware instructions. Processors of the logic processor 902 may be single-core or multi-core, and the instructions executed thereon may be configured for sequential, parallel, and/or distributed processing. Individual components of the logic processor optionally may be distributed among two or more separate devices, which may be remotely located and/or configured for coordinated processing. Aspects of the logic processor may be virtualized and executed by remotely accessible, networked computing devices configured in a cloud-computing configuration. In such a case, these virtualized aspects are run on different physical logic processors of various different machines, it will be understood.

Non-volatile storage device 904 includes one or more physical devices configured to hold instructions executable by the logic processors to implement the methods and processes described herein. When such methods and processes are implemented, the state of non-volatile storage device 904 may be transformed—e.g., to hold different data.

Non-volatile storage device 904 may include physical devices that are removable and/or built-in. Non-volatile storage device 904 may include optical memory (e.g., CD, DVD, HD-DVD, Blu-Ray Disc, etc.), semiconductor memory (e.g., ROM, EPROM, EEPROM, FLASH memory, etc.), and/or magnetic memory (e.g., hard-disk drive, floppy-disk drive, tape drive, MRAM, etc.), or other mass storage device technology. Non-volatile storage device 904 may include nonvolatile, dynamic, static, read/write, read-only, sequential-access, location-addressable, file-addressable, and/or content-addressable devices. It will be appreciated that non-volatile storage device 904 is configured to hold instructions even when power is cut to the non-volatile storage device 904.

Volatile memory 903 may include physical devices that include random access memory. Volatile memory 903 is typically utilized by logic processor 902 to temporarily store information during processing of software instructions. It will be appreciated that volatile memory 903 typically does not continue to store instructions when power is cut to the volatile memory 903.

Aspects of logic processor 902, volatile memory 903, and non-volatile storage device 904 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The terms "module," "program," and "engine" may be used to describe an aspect of computing system 900 typically implemented in software by a processor to perform a particular function using portions of volatile memory, which function involves transformative processing that specially configures the processor to perform the function. Thus, a module, program, or engine may be instantiated via logic processor 902 executing instructions held by non-volatile storage device 904, using portions of volatile memory 903. It will be understood that different modules, programs, and/or engines may be instantiated from the same application, service, code block, object, library, routine, API, function, etc. Likewise, the same module, program, and/or engine may be instantiated by different applications, services, code blocks, objects, routines, APIs, functions, etc. The terms "module," "program," and "engine" may encompass individual or groups of executable files, data files, libraries, drivers, scripts, database records, etc.

When included, display subsystem 906 may be used to present a visual representation of data held by non-volatile storage device 904. The visual representation may take the form of a graphical user interface (GUI). As the herein described methods and processes change the data held by the non-volatile storage device, and thus transform the state of the non-volatile storage device, the state of display subsystem 906 may likewise be transformed to visually represent changes in the underlying data. Display subsystem 906 may include one or more display devices utilizing virtually any type of technology. Such display devices may be combined with logic processor 902, volatile memory 903, and/or non-volatile storage device 904 in a shared enclosure, or such display devices may be peripheral display devices.

When included, input subsystem 908 may comprise or interface with one or more user-input devices such as a keyboard, mouse, touch screen, or game controller. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity; and/or any other suitable sensor.

When included, communication subsystem 1000 may be configured to communicatively couple various computing devices described herein with each other, and with other devices. Communication subsystem 1000 may include wired and/or wireless communication devices compatible with one or more different communication protocols. As non-limiting examples, the communication subsystem may be configured for communication via a wireless telephone network, or a wired or wireless local- or wide-area network. In some embodiments, the communication subsystem may allow computing system 900 to send and/or receive messages to and/or from other devices via a network such as the Internet.

The present disclosure further includes the following aspects. According to one aspect, a computer system is disclosed, which includes an electronic personal assistant application program executed on a client computing device, including a health recommender operatively coupled to a display and a health insurance retriever. In this aspect, the health recommender may be configured to identify at least one health condition of the user and determine a health recommendation, including at least a recommended health care service, at least based on the identified health condition, the user's electronic medical record, and the user's geolocation data. In this aspect, the health recommender may be configured to identify a plurality of health care providers that deliver the recommended health care service in a vicinity of the user. In this aspect, the health recommender may be configured to output on a display associated with the client computing device a graphical representation of the health recommendation, the plurality of health care providers, and an indication of whether the recommended health care service is covered by the user's health insurance plan at each of the plurality of health care providers. In this aspect, the health insurance retriever may be configured to retrieve the user's health insurance information, indicating whether the recommended health care service is covered by the user's health insurance plan at each of the plurality of health care providers. In this aspect, the health recommender may identify at least a health condition of a plurality of users in the vicinity of the user and may further determine the health recommendation based on the health condition of the plurality of users. In this aspect, the health recommender may determine an availability of the user to receive the recommended health care service based at least on a calendar. In this aspect, the health recommender may determine whether the user has at least a previous relationship to at least one of the plurality of health care providers, and output on the display a graphical indication of the previous relationship, if any. In this aspect, the health insurance information may include whether each of the plurality of health care providers is in-plan or out-of-plan for the user. In this aspect, the health insurance information may indicate user's coverage based on restrictions and requirements associated with the recommended health care service at each of the plurality of health care providers. In this aspect, the health insurance information may include a reimbursement benefit amount for the recommended health care service at each of the plurality of health care providers. In this aspect, the health recommender may determine scheduling information for each of the plurality of health care providers and outputs on the display an appointment scheduling interface with available timeslots at the plurality of recommended healthcare providers for the recommended health care service, receives a user selection of a timeslot and healthcare provider, and transmits the user selected timeslot and user ID of the user to the selected healthcare provider to make an appointment. In this aspect, the health recommender may output on the display a graphical representation of the plurality of health care providers, including a map indicating the location of the plurality of health care providers, and a route to at least one of the health care providers.

According to another aspect of the present disclosure, a method for outputting a health recommendation is disclosed, the method including identifying at least one health condition of the user; determining a location of the user; determining a health recommendation, including at least a recommended health care service, at least based on the identified health condition, the user's electronic medical record, and the user's geolocation data; identifying a plurality of health care providers that deliver the recommended health care service in a vicinity of the location of the user; retrieving the user's health insurance information, indicating whether the recommended health care service is covered by the user's health insurance plan at each of the plurality of health care providers; determining whether the recommended health care service is covered by the user's health insurance plan at each of the plurality of health care providers; and outputting on a display associated with the client computing device a graphical representation of the health recommendation, the plurality of health care providers, and an indication of whether the recommended health care service is covered by the user's health insurance plan at each of the plurality of health care providers. In this aspect, the method may further comprise identifying at least a health condition of a plurality of users in the vicinity of the user and further determines the health recommendation based on the health condition of the plurality of users. In this aspect, the method may further comprise determining an availability of the user to receive the recommended health care service based at least on a calendar. In this aspect, the determining of whether the recommended health care service is covered by the user's health insurance plan at each of the plurality of health care providers may further include determining that the recommended health care service is included in the benefits of the user's health insurance plan, determining that the recommended health care service is excluded from the benefits, or determining that the recommended health care service is partially included in the benefits. In this aspect, the determining of whether the recommended health care service is covered by the user's health insurance plan at each of the plurality of health care providers may include determining restrictions and requirements that are associated with the recommended health care service at each of the plurality of health care providers. In this aspect, the health insurance information may include a reimbursement benefit amount for the recommended health care service at each of the plurality of health care providers. In this aspect, the health insurance information may include a total coast for the recommended health care service at each of the plurality of health care providers less the reimbursement benefit amount, equaling a net cost for the user. In this aspect, the method may further comprise determining scheduling information for each of the plurality of health care providers and outputting on the display an appointment scheduling interface with available timeslots at the plurality of recommended healthcare providers for the recommended health care service, receiving a user selection of a timeslot and healthcare provider, and transmitting the user selected timeslot and user ID of the user to the selected healthcare provider to make an appointment. In this aspect, the method may further comprise outputting on the display a graphical representation of the plurality of health care providers, including a map indicating the location of the plurality of health care providers, and a route to at least one of the health care providers.

In another aspect, the method may further comprise correlating a plurality of medical and non-medical data from a plurality of client computing devices of a plurality of users with corresponding geolocation data to generate a first aggregated time and location-based history. In this aspect, the method may include correlating a plurality of medical data from electronic medical records from the plurality of users with corresponding geolocation data to generate a second aggregated time and location-based history. In this aspect, the method may include combining the first aggregated time and location-based history with the second aggregated time and location-based history and generate a global aggregated time and location-based history that includes time and location-based history that was correlated by the first correlator and the second correlator, and anonymize the global aggregated time and location-based history so as to form combined time and location-based data. In this aspect, the method may include determining the health recommendation based at least on the combined data, the user electronic medical record, and the identified health condition. In this aspect, the method may include outputting the health recommendation and combined data to the display. In this aspect, the medical and non-medical data may be associated with corresponding time-stamped geolocation data. In this aspect, the method may further comprise correlating a plurality of medical data and non-medical data of the user from the client computing device of the user with corresponding geolocation data and generate a user personal time and location-based history. In this aspect, the method may further comprise determining a health recommendation that is based at least on the user personal time and location-based history. Any or all of the above-described examples may be combined in any suitable manner in various implementations.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. A computing system comprising:
an electronic personal assistant application program executed on a client computing device configured to:
passively monitor a geolocation of the client computing device to obtain geolocation data and associated time data for a user for each of a plurality of geolocations; and
communicate the geolocation data and associated time data to a server system over a communications network for each of the plurality of geolocations;
the application program including:
a health recommender operatively coupled to a display and a health insurance retriever, the health recommender being configured to:
retrieve an electronic medical record of the user and a personal time and location-based history comprising a combined time and geolocation data of the user that is based, at least in part, on the geolocation data and associated time data communicated to the server system for each of the plurality of geolocations;
identify a differential diagnosis of a plurality of potential health conditions of the user listed in an order of likelihood and determine a health recommendation, including at least a recommended health care service, at least based on the identified potential health conditions, the electronic medical record of the user, and the personal time and location-based history of the user, the order of likelihood taking into account a time and location-based history of multiple users retrieved by the application program from the server system;
identify a plurality of health care providers that deliver the recommended health care service in a vicinity of the user; and
output, on the display associated with the client computing device, a graphical representation of the health recommendation for a potential health condition identified as highest ranked in the order of likelihood, the plurality of potential health conditions of the user listed in the order of likelihood, the plurality of health care providers, and an indication of whether the recommended health care service is covered by a health insurance plan of the user at each of the plurality of health care providers; and
the health insurance retriever configured to retrieve health insurance information of the user, indicating whether the recommended health care service is covered by the health insurance plan of the user at each of the plurality of health care providers.

2. The computing system of claim 1, wherein the health recommender identifies at least a health condition of a plurality of users in the vicinity of the user and further determines the health recommendation based on the health condition of the plurality of users.

3. The computing system of claim 1, wherein the health recommender determines an availability of the user to receive the recommended health care service based at least on a calendar.

4. The computing system of claim 1, wherein the health recommender determines whether the user has at least a previous relationship to at least one of the plurality of health care providers, and output on the display a graphical indication of the previous relationship, if any.

5. The computing system of claim 1, wherein the health insurance information includes whether each of the plurality of health care providers is in-plan or out-of-plan for the user.

6. The computing system of claim 1, wherein the health insurance information indicates user's coverage based on restrictions and requirements associated with the recommended health care service at each of the plurality of health care providers.

7. The computing system of claim 1, wherein the health insurance information includes a reimbursement benefit amount for the recommended health care service at each of the plurality of health care providers.

8. The computing system of claim 1, wherein the health recommender determines scheduling information for each of the plurality of health care providers and outputs on the display an appointment scheduling interface with available timeslots at the plurality of health care providers for the recommended health care service, receives a user selection of a timeslot and healthcare provider, and transmits the user selected timeslot and user ID of the user to the selected healthcare provider to make an appointment.

9. The computing system of claim 1, wherein the health recommender outputs on the display a graphical representation of the plurality of health care providers, including a map indicating the location of the plurality of health care providers, and a route to at least one of the health care providers.

10. A computer method, comprising:
passively monitoring a geolocation of a client computing device to obtain geolocation data and associated time data for a user for each of a plurality of geolocations;
communicating the geolocation data and associated time data to a server system over a communications network for each of the plurality of geolocations;
retrieving an electronic medical record of the user and a personal time and location-based history comprising a combined time and geolocation data of the user that is based, at least in part, on the geolocation data and associated time data communicated to the server system for each of the plurality of geolocations;
identifying a differential diagnosis of a plurality of potential health conditions of the user listed in an order of likelihood;
determining a location of the user;
determining a health recommendation, including at least a recommended health care service, at least based on the identified potential health conditions, the electronic medical record of the user, and the personal time and location-based history of the user, the order of likelihood taking into account a time and location-based history of multiple users retrieved by an application program from the server system;
identifying a plurality of health care providers that deliver the recommended health care service in a vicinity of the location of the user;
retrieving health insurance information of the user, indicating whether the recommended health care service is covered by a health insurance plan of the user at each of the plurality of health care providers;
determining whether the recommended health care service is covered by the health insurance plan of the user at each of the plurality of health care providers; and
outputting, on a display associated with the client computing device, a graphical representation of the health recommendation for a potential health condition identified as highest ranked in the order of likelihood, the plurality of potential health conditions of the user listed in the order of likelihood, the plurality of health care providers, and an indication of whether the recommended health care service is covered by the health insurance plan of the user at each of the plurality of health care providers.

11. The method of claim 10, further comprising:
identifying at least a health condition of a plurality of users in the vicinity of the user and further determines the health recommendation based on the health condition of the plurality of users.

12. The method of claim 10, further comprising:
determining an availability of the user to receive the recommended health care service based at least on a calendar.

13. The method of claim 10, wherein
the determining of whether the recommended health care service is covered by the user's health insurance plan at each of the plurality of health care providers includes determining that the recommended health care service is included in benefits of the user's health insurance plan, determining that the recommended health care service is excluded from the benefits, or determining that the recommended health care service is partially included in the benefits.

14. The method of claim 10, wherein
the determining of whether the recommended health care service is covered by the user's health insurance plan at each of the plurality of health care providers includes determining restrictions and requirements that are associated with the recommended health care service at each of the plurality of health care providers.

15. The method of claim 10, wherein
the health insurance information includes a reimbursement benefit amount for the recommended health care service at each of the plurality of health care providers.

16. The method of claim 15, wherein
the health insurance information includes a total cost for the recommended health care service at each of the plurality of health care providers less the reimbursement benefit amount, equaling a net cost for the user.

17. The method of claim 10, further comprising:
determining scheduling information for each of the plurality of health care providers and outputting on the display an appointment scheduling interface with available timeslots at the plurality of health care providers for the recommended health care service, receiving a user selection of a timeslot and healthcare provider, and transmitting the user selected timeslot and user ID of the user to the selected healthcare provider to make an appointment.

18. The method of claim 10, further comprising:
outputting on the display a graphical representation of the plurality of health care providers, including a map indicating the location of the plurality of health care providers, and a route to at least one of the health care providers.

19. The method of claim 10, further comprising:
correlating a plurality of medical data and non-medical data from a plurality of client computing devices of a plurality of users with corresponding geolocation data to generate a first aggregated time and location-based history;
correlating a plurality of medical data from electronic medical records from the plurality of users with corresponding geolocation data to generate a second aggregated time and location-based history,
combining the first aggregated time and location-based history with the second aggregated time and location-based history and generate a global aggregated time and location-based history that includes time and location-based history that was correlated, and anonymize the global aggregated time and location-based history so as to form combined time and location-based data, and
determining the health recommendation based at least on the combined data, the electronic medical records from the plurality of users, and the identified health condition; and
outputting the health recommendation and combined data to the display,
wherein the medical data and non-medical data are associated with corresponding time-stamped geolocation data.

20. The method of claim 19, further comprising:
correlating a plurality of medical data and non-medical data of the user from the client computing device of the user with corresponding geolocation data and generate a user personal time and location-based history, and
determining the health recommendation based at least on the user personal time and location-based history.

* * * * *